United States Patent
Jachmann et al.

(10) Patent No.: US 10,488,486 B2
(45) Date of Patent: Nov. 26, 2019

(54) NUCLEAR MAGNETIC RESONANCE TOOL CALIBRATION

(71) Applicant: Halliburton Energy Services, Inc., Houston, TX (US)

(72) Inventors: Rebecca Corina Jachmann, Kingwood, TX (US); Jie Yang, Paoli, PA (US)

(73) Assignee: Halliburton Energy Services, Inc., Houston, TX (US)

( * ) Notice: Subject to any disclaimer, the term of this patent is extended or adjusted under 35 U.S.C. 154(b) by 449 days.

(21) Appl. No.: 14/787,968

(22) PCT Filed: May 30, 2013

(86) PCT No.: PCT/US2013/043345
§ 371 (c)(1),
(2) Date: Oct. 29, 2015

(87) PCT Pub. No.: WO2014/193386
PCT Pub. Date: Dec. 4, 2014

(65) Prior Publication Data
US 2016/0077183 A1    Mar. 17, 2016

(51) Int. Cl.
*G01R 33/58*    (2006.01)
*G01R 33/561*    (2006.01)

(52) U.S. Cl.
CPC ........ *G01R 33/586* (2013.01); *G01R 33/5617* (2013.01)

(58) Field of Classification Search
None
See application file for complete search history.

(56) References Cited

U.S. PATENT DOCUMENTS

| | | | |
|---|---|---|---|
| 4,866,386 A | 9/1989 | Sattin | |
| 4,893,081 A | 1/1990 | Zur | |
| 5,107,215 A * | 4/1992 | Schaefer | G01R 33/583 |
| | | | 324/313 |
| 6,466,013 B1 * | 10/2002 | Hawkes | G01N 24/081 |
| | | | 324/303 |
| 6,512,372 B1 * | 1/2003 | Ikezaki | G01R 33/56581 |
| | | | 324/307 |
| 6,717,404 B2 | 4/2004 | Prammer | |
| 2004/0027122 A1 | 2/2004 | Heaton et al. | |
| 2004/0090230 A1 | 5/2004 | Appel et al. | |

(Continued)

FOREIGN PATENT DOCUMENTS

WO    WO-2014193386 A1    12/2014

OTHER PUBLICATIONS

"Australian Application Serial No. 2013390618, First Examiner Report dated Jul. 4, 2016", 5 pgs.

(Continued)

*Primary Examiner* — Douglas X Rodriguez
(74) *Attorney, Agent, or Firm* — Gilliam IP PLLC

(57) ABSTRACT

Various embodiments include apparatus and methods to calibrate a nuclear magnetic resonance tool. Example calibration techniques may include using intended ninety degree pulses as a control mechanism to evaluate echo pulses from generating pulse sequences. Example calibration techniques may include comparing a sequence of measurement signals with a reference sequence. Additional apparatus, systems, and methods are disclosed.

21 Claims, 13 Drawing Sheets

(56) References Cited

U.S. PATENT DOCUMENTS

| | | | |
|---|---|---|---|
| 2005/0248342 A1 | 11/2005 | Rottengatter et al. | |
| 2011/0050227 A1 | 3/2011 | Barrett et al. | |
| 2011/0234220 A1* | 9/2011 | Mitchell | G01N 24/081 324/303 |
| 2012/0235677 A1* | 9/2012 | Blanz | G01N 24/081 324/303 |
| 2012/0286779 A1 | 11/2012 | Walsh et al. | |
| 2013/0234706 A1* | 9/2013 | Mandal | G01N 24/081 324/303 |

OTHER PUBLICATIONS

"Canadian Application Serial No. 2,909,873, Office Action dated Aug. 2, 2016", 4 pgs.
"European Application Serial No. 13885996.2, Office Action dated Oct. 30, 2015", 2 pgs.
"European Application Serial No. 13885996.2, Response filed Apr. 22, 2016 to Office Action dated Oct. 30, 2015", 18 pgs.
"International Application Serial No. PCT/US2013/043345, Response filed Mar. 27, 2015 to Written Opinion dated Feb. 27, 2014", 30 pgs.
"One Pulse NMR and Pulse Calibration—General Application", [online]. Tecmag. [archived on Jul. 5, 2004]. https://web.archive.org/web/20040705151631/http://www.tecmag.com/pdf/1Pulse.pdf, (Oct. 11, 2002), 2 pgs.
Mitchell, J., et al., "A rapid measurement of T1/T2T1/T2: The DECPMG sequence", *Journal of Magnetic Resonance*, 200(2), (Oct. 2009), 198-206.
Prammer, M. G., et al., "A New Multiband Generation of NMR Logging Tools", *SPE-49011-MS, SPE Annual Technical Conference and Exhibition*, Sep. 27-30, New Orleans, Louisiana, (1998), 1-7.
"Application Serial No. PCT/US2013/043345, International Preliminary Report on Patentability dated Sep. 17, 2015", 8 pgs.
"International Application Serial No. PCT/US2013/043345, International Search Report dated Feb. 27, 2014", 6 pgs.
"International Application Serial No. PCT/US2013/043345, Written Opinion dated Feb. 27, 2014", 8 pgs.
AU Application Serial No. 2017204581, Examination Report No. 1, dated Jan. 24, 2019, 5 pages.
Bernstein, et al., "Spin Echo Fast Recovery", Handbook of MRI Pulse Sequences, Amsterdam: Elsevier, Chapter 17, 2004, pp. 890-893.
Casanova, et al., "NMR in Inhomogeneous Fields", Single-Sided NMR, Berlin: Springer-Verlag, 2011, pp. 11-56.

* cited by examiner

```
┌─────────────────────────────────────────────────────────────────┐
│ GENERATE A NUMBER OF PULSE SEQUENCES FROM A NUCLEAR MAGNETIC    │
│ RESONANCE (NMR) TOOL IN A CALIBRATION PROCEDURE SUCH THAT A PULSE│
│ AMPLITUDE OF EACH PULSE SEQUENCE OF THE NUMBER OF PULSE SEQUENCES│
│ VARIES FROM A PULSE AMPLITUDE OF OTHER PULSE SEQUENCES OF THE   │
│                 NUMBER OF PULSE SEQUENCES                       │
└─────────────────────────────────────────────────────────────────┘
                                                            —1510
┌─────────────────────────────────────────────────────────────────┐
│ SUM ECHOES, FOR EACH PULSE SEQUENCE, OF AN ECHO TRAIN GENERATED BY│
│ THE RESPECTIVE PULSE SEQUENCE SUCH THAT A SUMMED ECHO IS FORMED  │
│                    FOR EACH PULSE SEQUENCE                      │
└─────────────────────────────────────────────────────────────────┘
                                                            —1520
┌─────────────────────────────────────────────────────────────────┐
│ COMPARE THE SUMMED ECHOES FROM GENERATING THE NUMBER OF PULSE   │
│ SEQUENCES SUCH THAT COMPARISON OF THE SUMMED ECHOES DETERMINES  │
│ AN IDENTIFIED PULSE SEQUENCE, ALONG WITH ITS PULSE AMPLITUDE, HAVING│
│         ITS RESPECTIVE SUMMED ECHO CLOSEST TO ZERO              │
└─────────────────────────────────────────────────────────────────┘
                                                            —1530
┌─────────────────────────────────────────────────────────────────┐
│ SELECT THE AMPLITUDE OF THE IDENTIFIED PULSE SEQUENCE TO BE THE │
│                    CALIBRATED 180° PULSE                        │
└─────────────────────────────────────────────────────────────────┘
                                                            —1540
┌─────────────────────────────────────────────────────────────────┐
│ USE THE CALIBRATED 180° PULSE TO DETERMINE A CALIBRATED 90° PULSE│
└─────────────────────────────────────────────────────────────────┘
                                                            — 1550
```

Fig. 15

```
┌─────────────────────────────────────────────────────────────────┐
│ SELECT AN INTENDED 90° PULSE AND AN INTENDED 180° PULSE, THE SELECTION│
│ HAVING AN AMPLITUDE CONSTRAINT DEFINED BY AN AMPLITUDE OF THE   │
│ INTENDED 180° PULSE BEING TWICE AN AMPLITUDE OF THE INTENDED 90° PULSE,│
│ WHEREIN IN EACH ITERATION AN OVERALL AMPLITUDE IS MODIFIED CHANGING│
│ AMPLITUDES OF THE INTENDED 90° PULSE AND THE INTENDED 180° PULSE│
│           WHILE MAINTAINING THE AMPLITUDE CONSTRAINT            │
└─────────────────────────────────────────────────────────────────┘
                                                            —1610
┌─────────────────────────────────────────────────────────────────┐
│ GENERATE A PULSE SEQUENCE INCLUDING THE INTENDED 90° PULSE AND THE│
│ INTENDED 180° PULSE FROM THE NMR TOOL SUCH THAT A PATTERN IS PROVIDED│
└─────────────────────────────────────────────────────────────────┘
                                                            —1620
┌─────────────────────────────────────────────────────────────────┐
│        GENERATE A RESPONSE SEQUENCE FROM THE ECHO PULSES        │
└─────────────────────────────────────────────────────────────────┘
                                                            —1630
┌─────────────────────────────────────────────────────────────────┐
│    COMPARE THE RESPONSE SEQUENCE TO A REFERENCE RESPONSE PATTERN│
└─────────────────────────────────────────────────────────────────┘
                                                            —1640
┌─────────────────────────────────────────────────────────────────┐
│ PROCEED TO A NEXT ITERATION UNTIL A CORRECT PATTERN OF THE RESPONSE│
│       SEQUENCE IS DETERMINED FROM THE COMPARISON                │
└─────────────────────────────────────────────────────────────────┘
                                                            —1650
```

Fig. 16

NUCLEAR MAGNETIC RESONANCE TOOL CALIBRATION

PRIORITY APPLICATIONS

This application is a U.S. National Stage Filing under 35 U.S.C. § 371 from International Application No. PCT/US2013/043345, filed on 30 May 2013, and published as WO 2014/193386 on 4 Dec. 2014, which application and publication are incorporated herein by reference in their entirety.

TECHNICAL FIELD

The present invention relates generally to apparatus and methods related to nuclear magnetic resonance.

BACKGROUND

Nuclear magnetic resonance (NMR) is used as a tool in a number of different technology areas to investigate different types of mediums. NMR can occur when the medium is subjected to a static magnetic field, $B_0$, and to an oscillating magnetic field, $B_1$. When subjected to an applied static magnetic field, polarization of nuclear magnetic spins of the medium occurs based on spin number of the medium and magnetic field strength. Applying an electromagnetic field to the medium in the static magnetic field can perturb the polarization established by the static magnetic field. In optimal measurements, the static magnetic field and the perturbing field are perpendicular to each other. Collected responses received from the medium related to the total magnetization of nuclear spins in the medium, in response to these applied fields, can be used to investigate properties of the medium, and may provide imaging of the medium. It is noted that magnetization is proportional to polarization.

Nuclear magnetic resonance measurements are created by the oscillation of excited nuclear magnetic spins in the transverse plane, that is, the direction perpendicular to the magnetic field. This oscillation eventually dies out and the equilibrium magnetization returns. The return process is referred to as longitudinal relaxation. The time constant, $T_1$, for nuclei to return to their equilibrium magnetization, $M_o$, is called the longitudinal relaxation time or the spin lattice relaxation time. The magnetization dephasing, that is losing coherence, along the transverse plane is given by the time constant $T_2$ and is called the spin-spin relaxation time. The loss of phase coherence can be caused by several factors including interactions between spins or magnetic gradients.

A widely used NMR measurement technique, designed by Carr, Purcell, Meiboom, and Gill and, hence, referred to as CPMG, uses a sequence of radio frequency pulses to produce spin echoes and counteract dephasing of the magnetization in the medium investigated. In the CPMG sequence, an initial pulse, commonly a 90° pulse, can be applied to tip the polarization into a plane perpendicular to the static magnetic field. To counter dephasing due to magnetic inhomogeneities, another pulse, a recovery pulse, commonly a 180° or other angle tipping pulse, is applied to return to phase, which produces a signal called an echo from the medium. Yet, after each return to phase, dephasing begins and another recovery pulse is applied for rephasing. Rephasing or refocusing is repeated many times in the CPMG sequence, while measuring each echo. The echo magnitude decreases with time due to a number of irreversible relaxation mechanisms. The CPMG sequence can have any number of echoes, where the time between each echo can be relatively short, for example, of the order of 1 ms or less or as long as 12 ms is used.

FIG. 1 illustrates use of a 90° tipping pulse and a sequence of 180° refocusing pulses. In this sequence, the ten 180° refocusing pulses cause ten echoes 107-1 ... 107-10, where the peak amplitudes of the echoes are equally spaced apart by a peak to peak time distance, TE, that corresponds to the equally spaced apart time distances of the refocusing pulses. Also indicated are an acquisition window for capturing the signal of an echo, a first echo $E_1$, a second echo $E_2$, and $A_0$. $A_0$ is the amplitude of the echo train at time zero. $A_0$ can be calculated by using an exponential decay fitting curve determined from a third echo $E_3$ to the last echo. $E_1$ and $E_2$ can be included if they are corrected. These echoes decay according to the $T_2$ of the medium. Once the nuclear spin population is fully recovered for the sequence, the medium can be probed again by another sequence.

Petrophysical information can be derived from NMR measurements, such as, but not limited to petrophysical properties of fluid containing porous media. Various properties that can be measured using an NMR logging tool include pore size, porosity, surface-to-volume ratio, formation permeability, and capillary pressure. For instance, the distribution of $T_2$ values can be used to estimate pore size. As noted above, $T_2$ is related to loss of phase coherence that occurs among spins, which can be caused by several factors. For example, magnetic field gradients in pores lead to different decay rates. Thereby different pore sizes in the formation produce a distribution of $T_2$ values, which is shown in the conversion of spin-echo decay data of NMR measurements. This distribution represents a "most likely" distribution of $T_2$ values that produce the echo train of the measurement. This distribution can be correlated with a pore size distribution when the rock is 100% water saturated. However, if hydrocarbons are present, the $T_2$ distribution will be altered depending on the hydrocarbon type, viscosity, and saturation. With proper calibration and account for hydrogen index of the fluids in the pore space, the area under a $T_2$ distribution curve is equal to total porosity. More precision in the evaluation of NMR data may be aided with increased acquisition of data from multiple NMR measurements.

A 90° pulse has the function of tipping the magnetization into the transverse plane, while a 180° pulse has the function of inverting the magnetization. A pulse has two characterizations: length in time, called duration, and amplitude. The pulse can be modulated by frequency and amplitude, which gives it a density. These two characterizations play off each other. A 90° pulse can be achieved by having the correct integrated amplitude. When a pulse intended to tip a sample 90° degrees has the wrong integration, it is no longer a true 90° pulse. When a pulse intended to tip a sample 90° degrees is not a true 90° pulse, the NMR signal is reduced. Therefore, in order to obtain the best signal-to-noise ratio (SNR), it is important that the intended 90° pulse has a correct shape, both in duration and density, to flip the magnetization by 90° degrees, as well as the intended 180° having a correct shape. Herein, pulses with certain intent that are not achieving their desired intent are designated by quotation marks. For example, "90" stands for a pulse which tips magnetization near 90° but not actually 90 degrees. Also, "180" stands for a pulse intending to be 180°, but the tipping angle is either larger or smaller than 180°. In general, the 180° pulse has twice the duration of the 90° pulse with the same amplitude. However, the 180° pulse need not be defined in this manner, and can be calibrated separately from a 90° pulse.

A current method of calibrating for optimal 90° flip in a magnetic resonance imaging logging tool can include running CPMG sequences as shown in FIGS. 2-5, in which amplitude is varied and the resulting $A_0$ values or echo amplitudes are compared. Alternatively, variation of pulse duration can be used.

The CPMG sequence is followed by a wait time, WT. This wait time is usually about 5 times the T1 of the solution. In pure water, the WT can be on the order of 12 to 15 seconds. Usually water is doped, lowering $T_1$, in the calibration tank, which can cause additional error and problems. Other substances, for example, glycerol and peanut oil, can be used to calibrate a tool.

In these calibration processes, correction for the first two echoes ($E_1$ and $E_2$) of the pulse train can also be found. A restriction on the calibration sample in these processes is that it has NMR active nuclei for the experiment. There are also limitations on how small the T2 can practically be. The hydrogen index of the calibration sample is also a useful piece of information.

The calibrations for the 90° and 180° pulses are performed iteratively in their respective current methods. Either the 90° calibration or the 180° calibration can be performed first. FIG. 2 shows a typical CPMG sequence for a conventional tool calibration in which an intended ninety degree amplitude is varied, while an intended one hundred eighty length and amplitude are held constant. A "180" pulse length and amplitude are chosen and held constant, while the "90" pulse is incremented through many different amplitudes. Having "90" pulse amplitudes varied, while "180" pulse amplitude is held constant provides a first stage. A best "90" from this first stage is then determined by determining the maximized $A_0$ or echo amplitude. The best "90" may be determined by curve fitting to find the highest $A_0$ or echo values. The determined best "90" pulse is then used in a sequence, where the "90" pulse properties are held constant and the "180" pulses are varied.

FIG. 3 shows a typical CPMG sequence for a conventional tool calibration in which an intended one hundred eighty amplitude is varied, while an intended ninety degree amplitude is held constant. Varying "180" pulse amplitude, while "90" pulse amplitude is held constant, provides a second stage to the procedure. A best "180" pulse is then determined by determining the maximized $A_0$ or echo amplitude. The best "180" pulse may be determined by curve fitting to find the highest $A_0$ or echo values. As noted above, stage 2 may be conducted to determine a best "90" pulse with stage 1 conducted to determine a best "180" pulse.

A few iterations of these sequences can be performed until the best "90" to "180" ratio is determined Then, an overall amplitude assessment can be conducted, where the sequence is scaled incrementally. FIG. 5 shows a typical calibration method that compares $A_0$, $E_1$, and $E_2$ values, which are fit to 2-degree polynomials. The $A_0$ values can be solved for the best amplitude (AM) or strength $B_1$ of the CPMG pulse. This results in a determination of an overall amplitude to be used down hole. In addition, $E_1$ and $E_2$ correction factors can be calculated.

BRIEF DESCRIPTION OF THE DRAWINGS

FIG. 15 shows features of an example method to calibrate a nuclear magnetic resonance tool, in accordance with various embodiments.

FIG. 16 shows features of an example method to calibrate a nuclear magnetic resonance tool, in accordance with various embodiments.

DETAILED DESCRIPTION

The following detailed description refers to the accompanying drawings that show, by way of illustration and not limitation, various embodiments in which the invention may be practiced. These embodiments are described in sufficient detail to enable those skilled in the art to practice these and other embodiments. Other embodiments may be utilized, and structural, logical, and electrical changes may be made to these embodiments. The various embodiments are not necessarily mutually exclusive, as some embodiments can be combined with one or more other embodiments to form new embodiments. The following detailed description is, therefore, not to be taken in a limiting sense.

In various embodiments, processes are provided to find an optimal 90° magnetization tipping pulse and an optimal 180° magnetization tipping pulse in calibration for a NMR logging tool. Finding optimal 90° and 180° magnetization tipping pulses can include processes to find optimal 90° and 180° pulse duration or amplitude for NMR down-hole tools that are operable in a wire-line tool, a drilling tool, or a sustaining type tool, along with lab testing.

Figure 1:
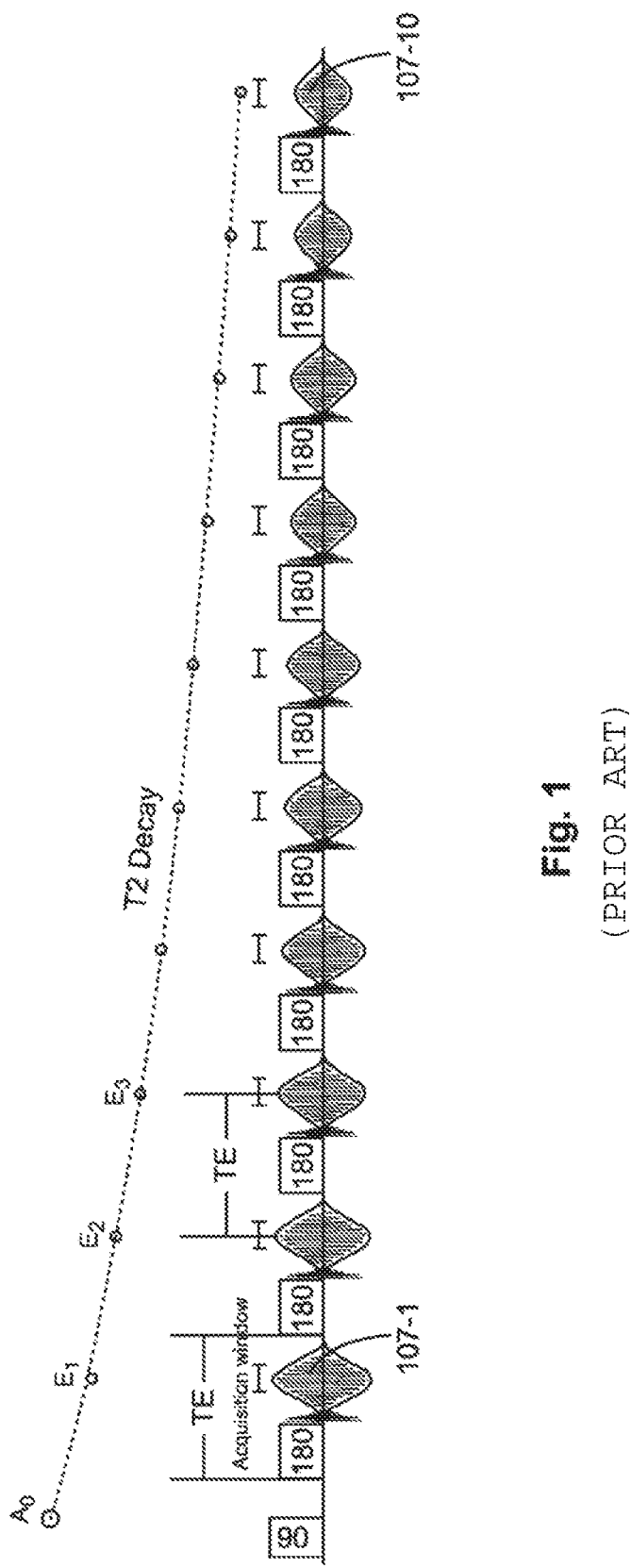
FIG. 1 illustrates use of a 90° tipping pulse and a sequence of 180° refocusing pulses, in accordance with various embodiments.
Figure 2:
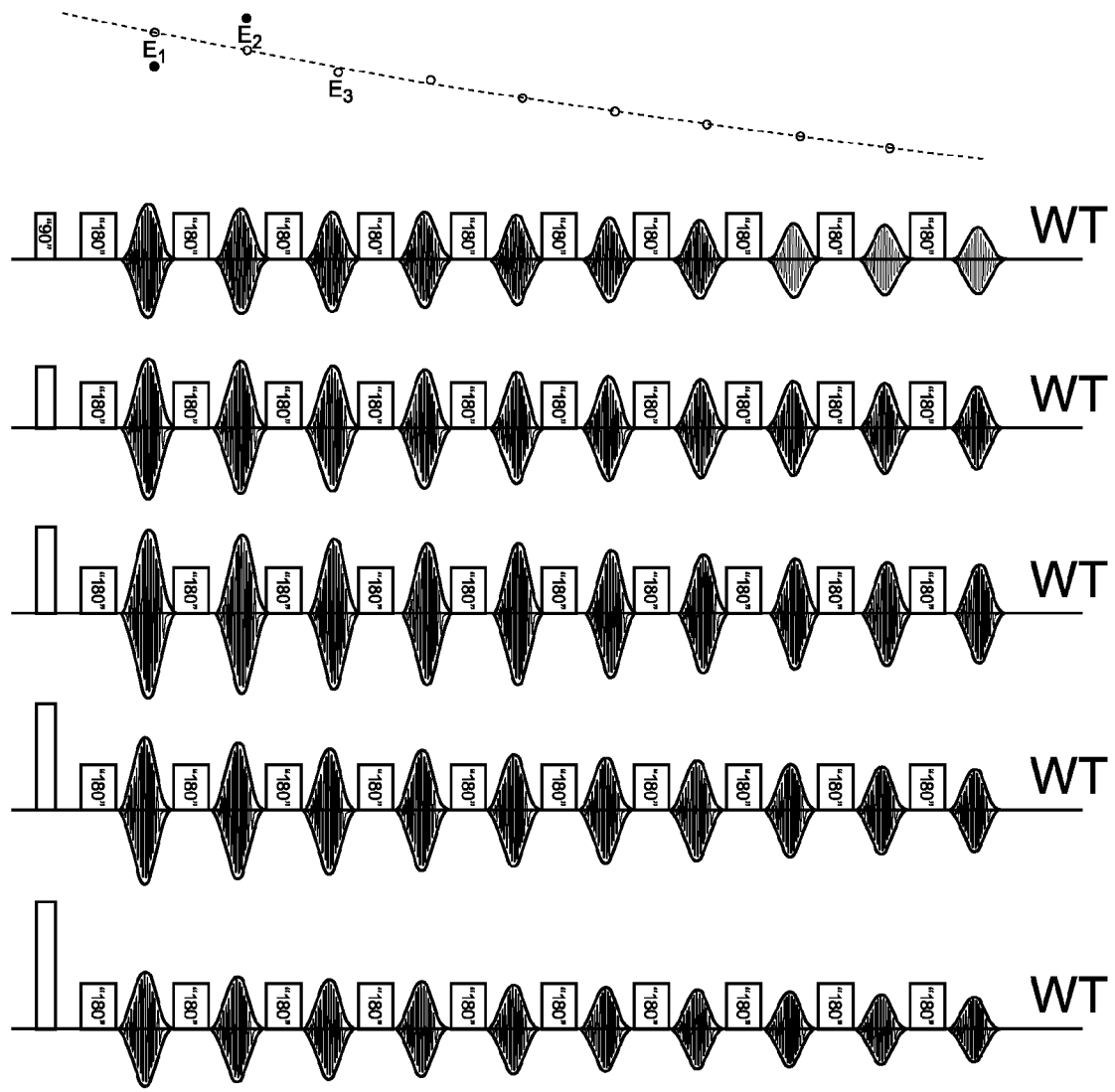
FIG. 2 shows a typical CPMG sequence for a conventional tool calibration in which an intended ninety degree amplitude is varied, while an intended one hundred eighty amplitude and duration are held constant.
Figure 3:
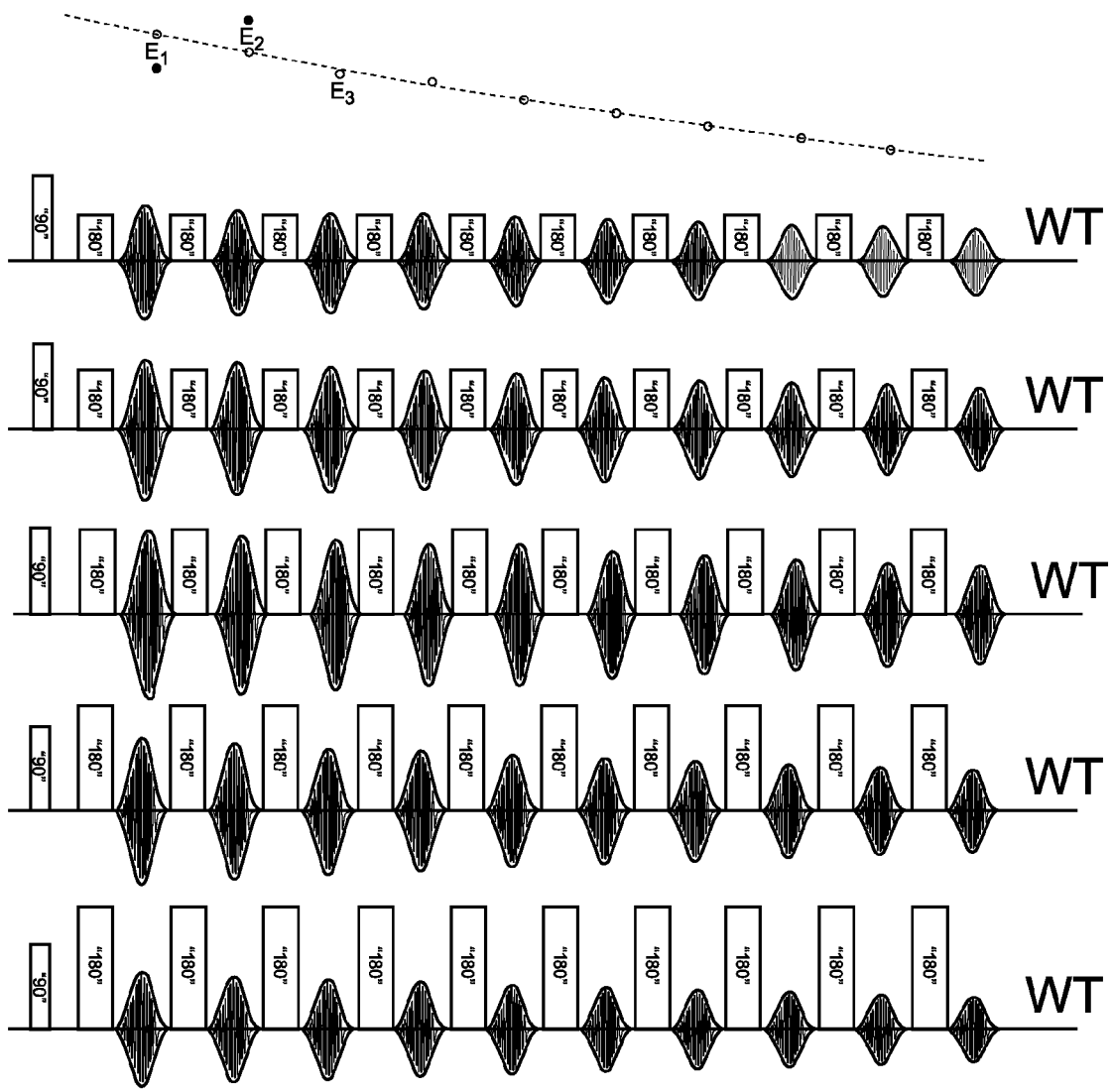
FIG. 3 shows a typical CPMG sequence for a conventional tool calibration in which an intended one hundred eighty amplitude is varied, while an intended ninety degree amplitude is held constant.
Figure 4:
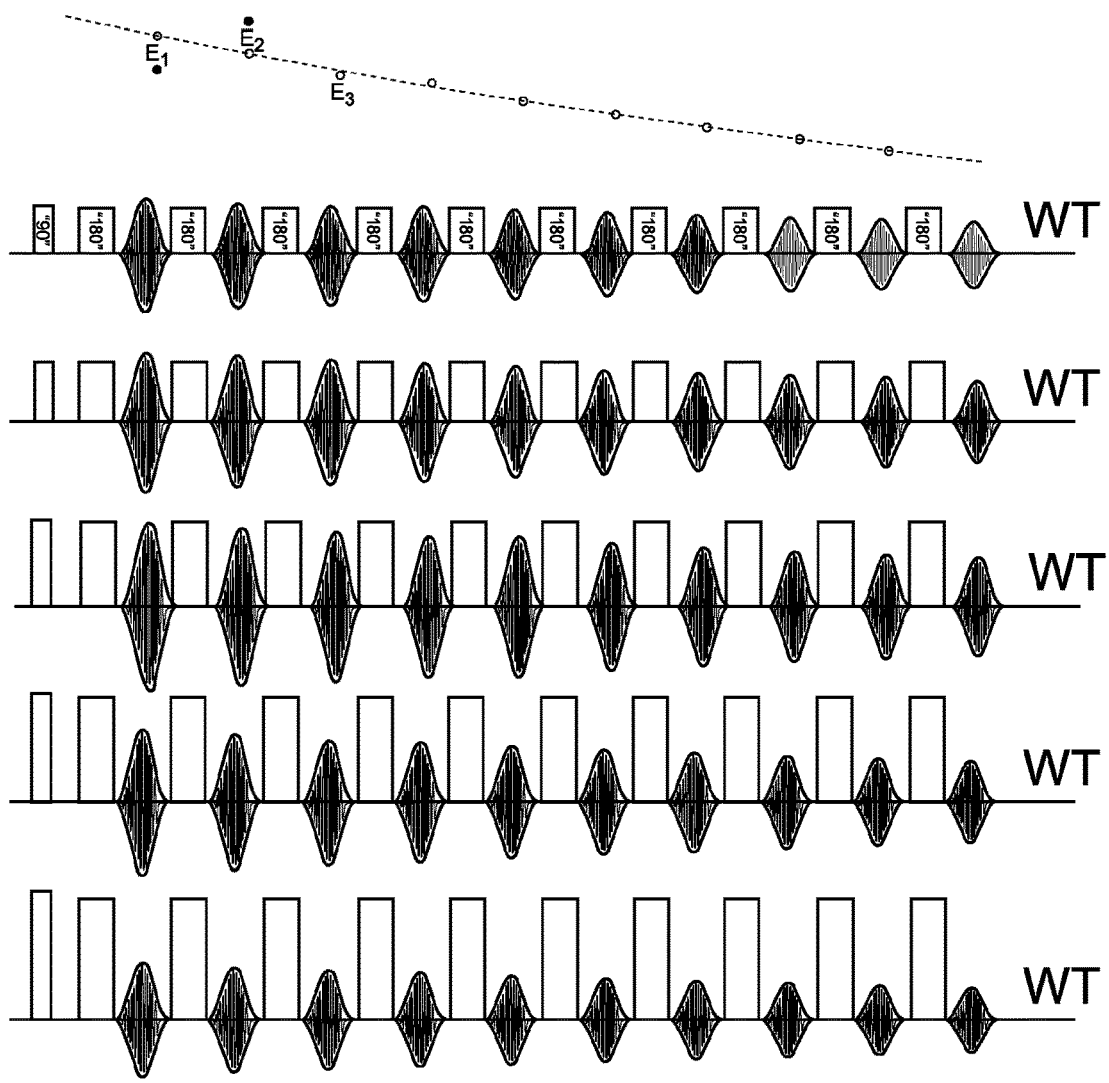
FIG. 4 shows a few iterations of a typical CPMG sequence for a conventional tool in which an overall amplitude assessment is performed, where the sequence is scaled incrementally, resulting in an overall amplitude to be used down hole.
Figure 5:
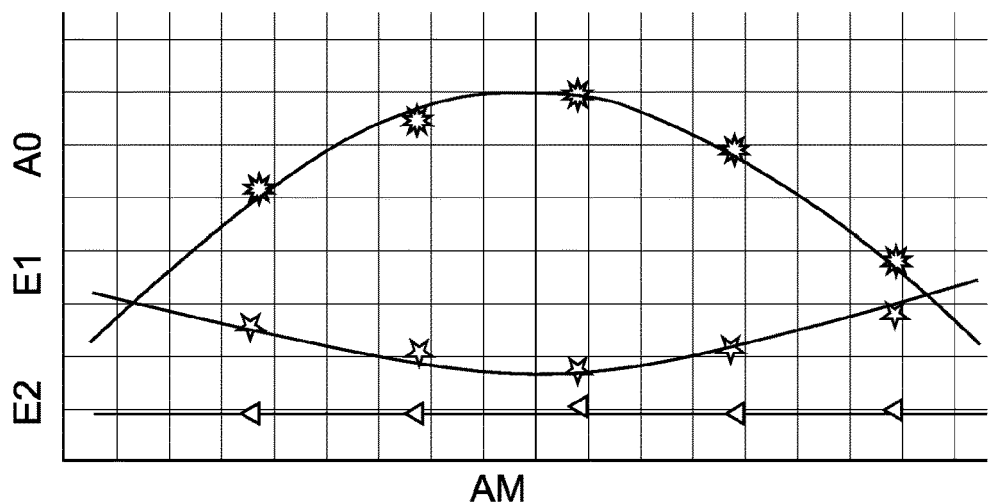
FIG. 5 shows a typical calibration method that compares $A_0$, $E_1$, and $E_2$ values, which are fit to 2-degree polynomials.
Figure 6:
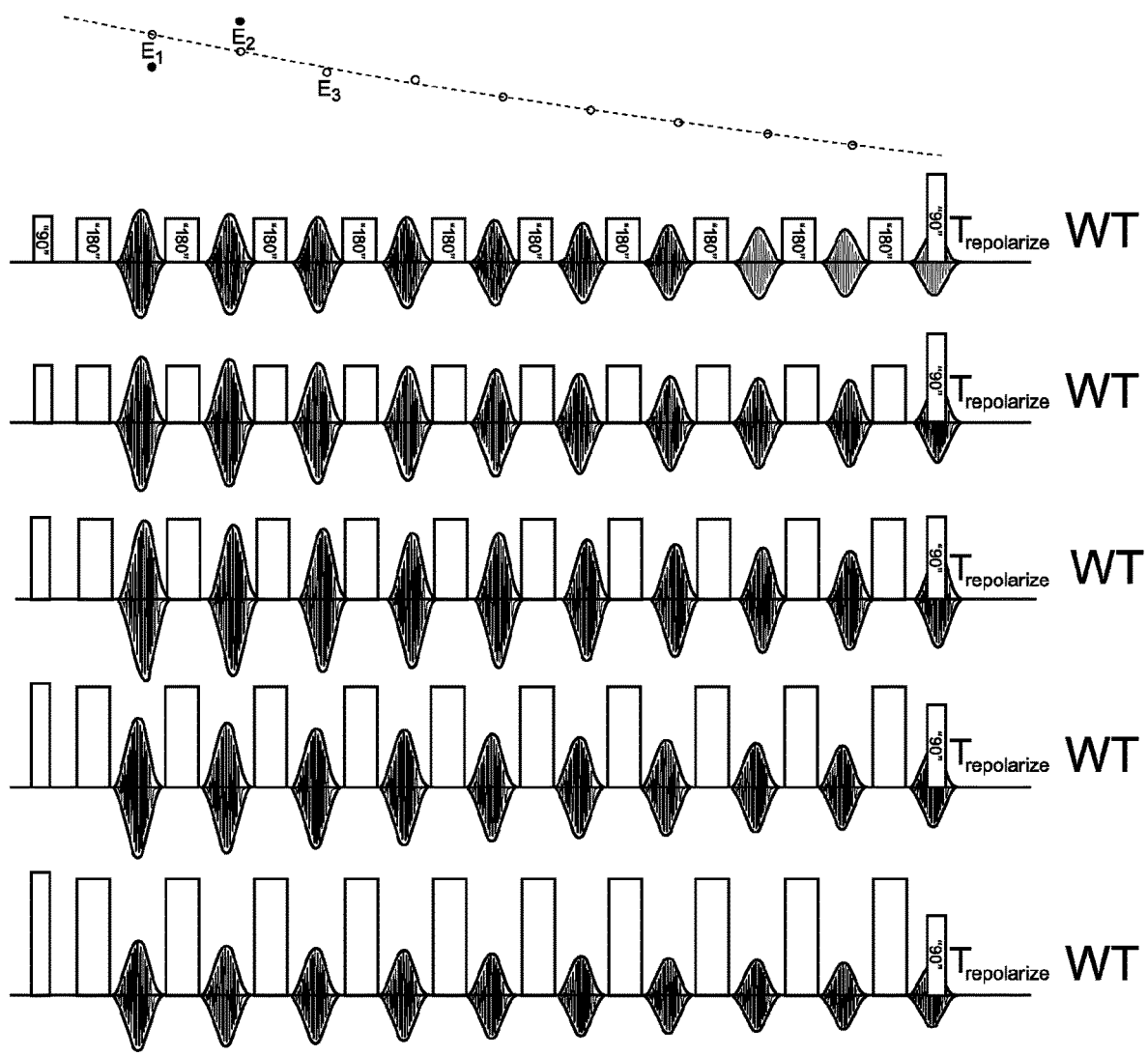
FIG. 6 shows a CPMG sequence for tool calibration using a recovery pulse at the end of the CPMG sequence, in accordance with various embodiments.

FIG. 6 shows an example embodiment of a calibration process using a recovery pulse. In various embodiments, a recovery pulse is used at the end of the calibration sequence. A CPMG sequence can be implemented as a calibration sequence for tool calibration with a recovery pulse added. This recovery pulse provides repolarization, which can reduce the needed WT for full recovery. The recovery can be realized as a 90 degree pulse applied at the time that corresponds to the maximum amplitude of the echo that would follow the last refocusing pulse of the sequence. The recovery pulse can be applied having the opposite orientation as the tipping pulse. This enhancement to the measurement process can be on the order of a few milliseconds to near the full WT depending on the number of echoes used in the sequence. Fewer echoes allows for shorter WTs. Calibration can be determined by comparing $A_0$ values from sequences with different "90"/"180" amplitudes. Any number of "180" pulses may be used.

The tipping pulse can be a 90 degree pulse, the refocusing pulses can be 180 degree pulses in a sequence of n refocusing pulses that are followed by echoes, an end refocusing 180 degree pulse, and the recovery pulse can be a 90 degree pulse added at the end of the echo train sequence. The tipping pulse, the refocusing pulses, and the recovery pulse are not limited to a 90° pulse, 180° pulses, and a 90° pulse, respectively. For example, a 45° tipping pulse, 135° refocusing pulses, and a 90° recovery pulse can be used to reduce the wait between sequences by providing a recovery starting point that is closer to the equilibrium magnetism than in a CPMG sequence having the same number of refocusing pulses. The total recovery time is assigned a percent of signal recovered, since true full recovery is infinitely long. There may be minimal error due to only obtaining 97% recovery.

Figure 7:
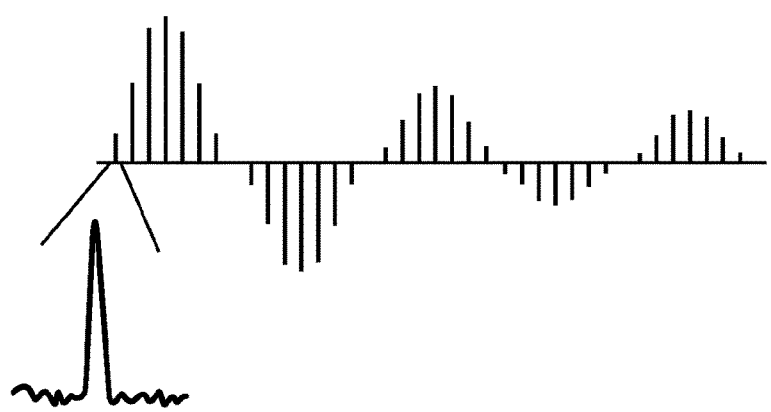
FIG. 7 shows a calibration using a nutation curve for a tool operable downhole, in accordance with various embodiments.

FIG. 7 shows a calibration using a nutation curve for a downhole type tool. This can be realized for a high field NMR tool with respect to free induction decay (FID). A nutation curve is a sequence which repeats a single pulse with either varying amplitude or width. The FID is acquired after each pulse. The response signal can be Fourier transformed into the frequency domain, though such a transformation is not required. The signal amplitude rises with increased transmitter amplitude. As the transmitter amplitude passes the true 90°, the signal starts to decrease until it is nullified. From the point at which the signal is nulled, the signal becomes "negative" and then rises once again to go through this cycle again. This cycle continues to be repeated. In various embodiments, the nutation process can be applied to downhole tools operable to acquire a FID.

In various embodiments, a calibration process includes a sequence of the same type of pulses, where each pulse is followed by a FID time period. The sequence can include N pulses, where each pulse has the same transmitter amplitude. For example, Such a calibration process may include a sequence of 4 pulses, all with the same transmitter amplitude. The type of pulses can be "90 pulses. For understanding, substantially homogenous B0 and B1 fields can be examined first utilizing a series of "90 pulses. This procedure may apply to some down-hole tools but not all. A key to utilizing a rendition of this procedure may be based on the FID signal lasting substantially longer than N×["90" pulse ringing-acquisition], where N=the number of pulses used. For example shown, N=4 for the sequence of 4 pulses. This rendition of calibration acquires the FID of the signal, with a sequence of four "90" pulses: "90"-FID-"90"-FID-"90"-FID-"90"-FID. This calibration experiment is not limited to using four "90" pulses, but the number of pulses set to 4 may be the most logical sequence. In this procedure, 90 degree pulse calibration is achieved but no correction for E1 or E2 is provided. When calibrating, a particular response pattern is expected: maximum signal-0-negative maximum signal-0. An error in the "90" pulse, either intensity or duration, is magnified by the end of the sequence. A desired pattern for a 90 degree pulse calibration using 4 pulses is demonstrated in FIGS. 8A-8D.

Figure 8A:
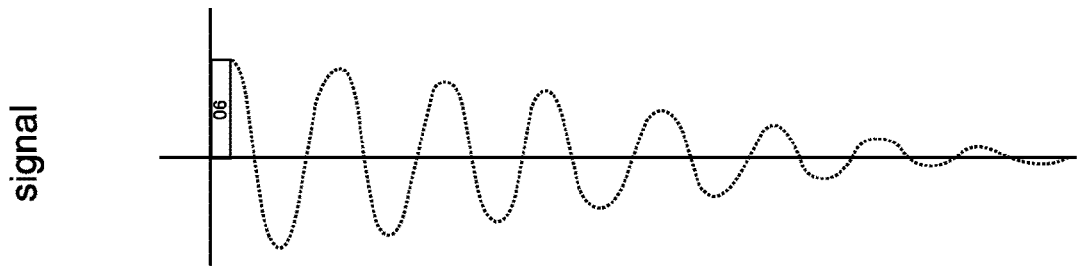
FIGS. 8A-8D show an example of a free induction decay after a ninety degree pulse slightly off resonance, a free induction decay on resonance, a ninety degree calibration, in accordance with various embodiments, and when the calibration embodiment is not using a perfect intended ninety degree pulse.
Figure 8B:
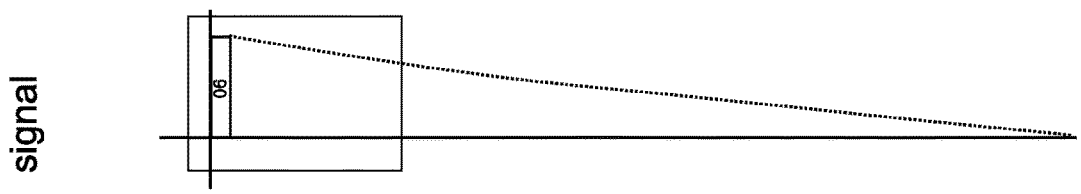
Figure 8C:
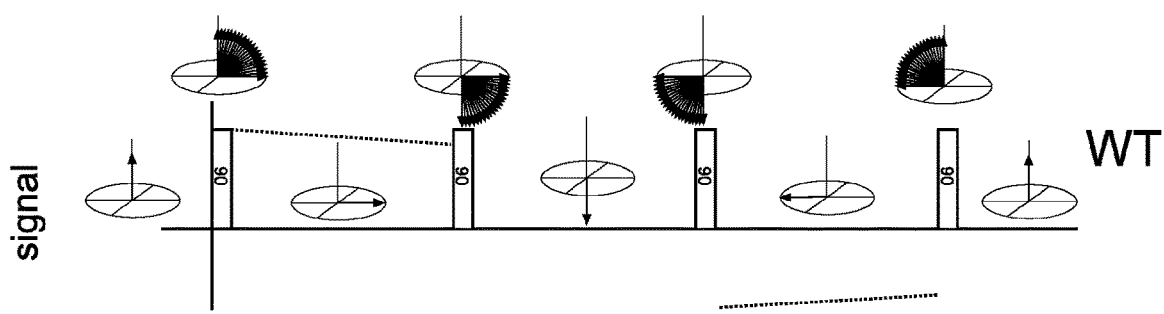
Figure 8D:
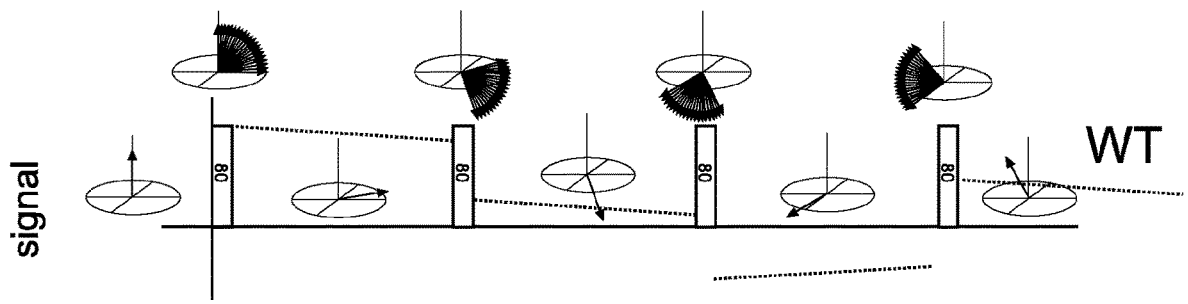

FIGS. 8A-8D show an example of a ninety degree calibration using four "90" pulses, where each "90" pulse is followed by a FID time period. FIG. 8A shows an example of a FID signal of a single true 90° pulse off the carrier frequency. FIG. 8B shows the FID signal of a single true 90° pulse on the resonant frequency. FIG. 8C shows the beginning of the FID. This rendition in FIG. 8C shows the case of a true ninety. The first 90 produces maximum signal, a second 90 kills all signal, a third 90 inverts the signal, and a maximal negative signal is observed, then a forth 90 returns the magnetization to the z direction and no signal is observed. This sequence is followed by a minimal WT to fully recover signal loss. FIG. 8D shows a case where the intended pulse is not a true 90, but is a "90". In this figure, the specific case of an 80 degree pulse is demonstrated. The signal response of FIG. 8D differs from the signal response shown in FIG. 8C. In the rendition shown in FIG. 8D, the first time period signal is not maximum, the second time period signal is above zero, the third time period is not maximum negative, and the fourth time period shows a significant amount of signal. This incorrect pattern provides an alert that the "90" pulse is not optimal. This alert can be provided as a display to a user. The display may be a video screen or a print of the information or alert. This alert can be generated within a machine or provided to a machine such as a computer. An automated program may be used to evaluate the calibration experiment.

The calibration can include an optimization scheme in which the current or duration of the pulses are varied. This scheme can test each of the time periods post "90" pulse separately or the summation of any to all of the 4 time periods post "90" pulse. Summing the signal from all 4 time periods should be equal to zero at optimal 90° tipping. The optimization scheme could include a polynomial fit or a search for the optimal point such as using the Nelder-Mead method, but is not limited to any particular method.

The type of pulse can be a one hundred eighty degree pulse. A scheme of "180"-FID-"180"-FID-"180"-FID-"180"-WT can be used to find the true 180° pulse. The ideal signal response for a 180 pulse is 0-0-0-0. When signal arises, a user or automated program can determine that the "180" is not perfect. The calibration can include an optimization scheme for the one hundred eighty degree pulse similar to the optimization scheme for the ninety degree pulse.

The type of pulse in a calibration scheme is not limited to 90-degree and 180-degree pulses. For example, a 135-degree pulse may be used. Other types of pulses that give a unique pattern from repeating the pulse followed by an acquisition period can be calibrated by utilizing the techniques discussed above. If the signal requires a rephased echo or the instrument cannot collect a FID, there are several techniques that can be implemented.

Figure 9:
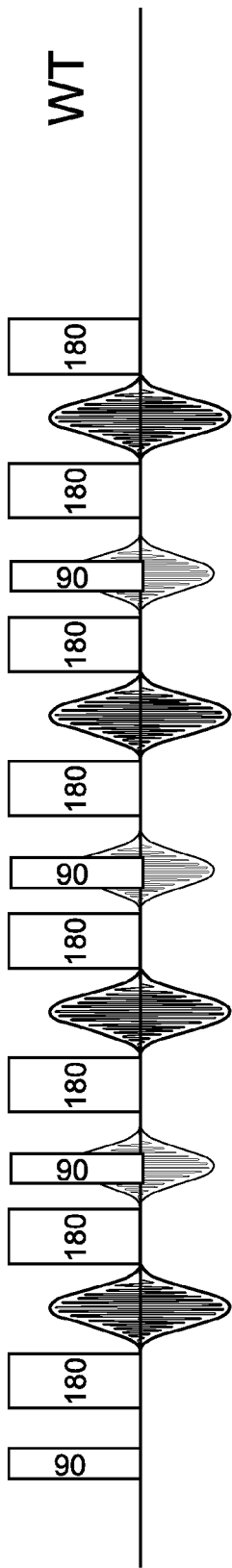
FIG. 9 shows a hybrid of a ninety degree calibration sequence that uses one hundred eighty degree recovery pulses, in accordance with various embodiments.

If the field homogeneity of the tool is not sufficient to sustain a long FID, a recovery echo type sequence can be utilized as demonstrated in FIG. 9. FIG. 9 shows a hybrid of a "90"-FID-"90"-FID-"90"-FID-"90"-FID calibration sequence that uses "180" recovery pulses when a $T_2$ is too fast to capture a FID effectively or the tool cannot acquire a FID. A "90" pulse excites the sample followed by a "180." After a second "180" pulse, a "90" pulse is used and then the pattern continues. Similar to the calibration technique discussed above, the expected response would be: maximum signal-0-negative maximum signal-0. This signal observed can be the peak of the echo or the integration of the echo signal. An optimization scheme can be used in which the current or duration of the pulses are varied. Each of the time periods post "90" pulse can be tested separately or the summation of any to all of the 4 time periods post "90" pulse can be tested in the optimization scheme. Summing the signal from all 4 time periods should be equal to zero at optimal 90 tipping. The optimization scheme could include a polynomial fit or a search for the optimal point such as using the Nelder-Mead method, but is not limited to any particular method.

Due to stimulated echoes, caused by an inhomogeneous $B_1$ field, the first echo may not behave in the expected way. Hence, there may be a need for a correction. The second echo may also have a severe stimulated echo problem. Using more echoes, above 3, alleviates this problem. Also, with the acquisition of $E_2$ and a short echo train, the correction for both echoes can be found. Otherwise, once the correct 90° pulse has been determined, a full echo train can be run and the $E_1$ and $E_2$ corrections found. The correction can be generated as a scaling factor to correct a measurement relative to its predicted location. An optimization scheme for this type of sequence can utilize $E_3$ and higher. These echoes can have their peak values checked, the peak values summed, the echoes integrated, or the echo integrations summed The current can be modified in an iterative manner such that the best "90" can be found.

Figure 10:
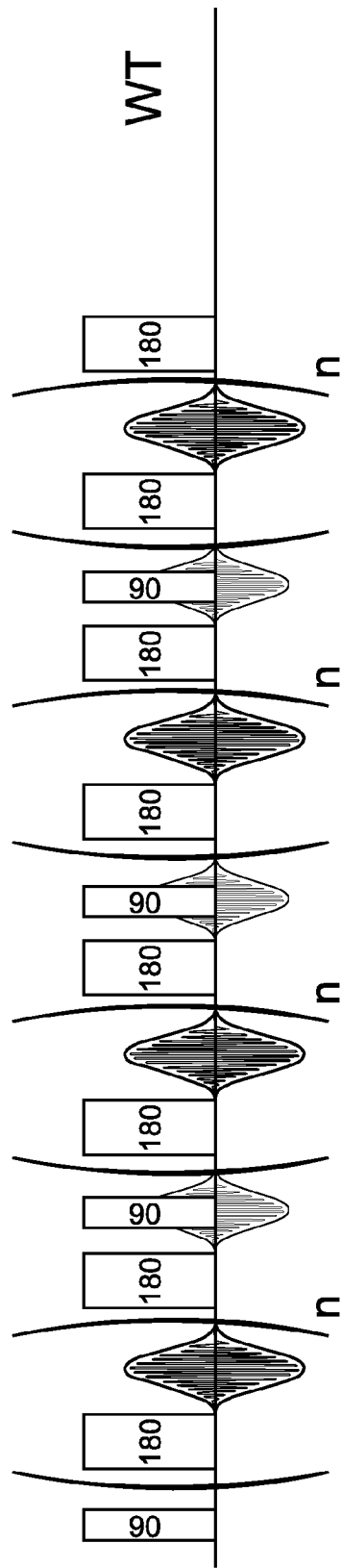
FIG. 10 shows a hybrid of a ninety degree calibration sequence that uses multiple one hundred eighty degree recovery pulses between ninety degree pulses, in accordance with various embodiments.

A technique to provide a determination of the 180° pulse can include varying the pulse amplitude such that the sum of echoes at the end of the train is as close to 0 as possible. The amplitude which gives nearest 0 in this case is considered to be the 180° pulse amplitude. FIG. 10 shows a hybrid of a ninety degree calibration sequence that uses multiple one hundred eighty degree recovery pulses between ninety degree pulses. With a known 180° pulse, the 90° pulse can then be found by using the sequence "90"-(180-echo)$_n$-180 -"90"-(180-echo)$_n$-180 -"90"-(180-echo)$_n$-180 -"90"-(180-echo)$_n$-180 and varying the amplitude of the "90" until the correct patterning is achieved. Each "90" is applied at a time that would correspond to the peak of an echo following the 180° pulse after the respective-(180-echo)$_n$ sequence.

Another technique can include a procedure to simultaneously calibrate the 90° pulse and the 180° pulse by constraining their amplitudes such that Amp(90°)×2=Amp (180°). Then, the overall amplitude can be modified until the correct patterning is found.

In various embodiments, calibration techniques use a multiple "90" degree sequence and magnetization recovery at the end of each sequence. These techniques allow for short calibration time and enhancement on "90" time calibration providing more accuracy than calibration methods that use a single 90 degree sequence in which either amplitude or duration is changed and the resultant change in CPMG SNR is observed.

Figure 11:
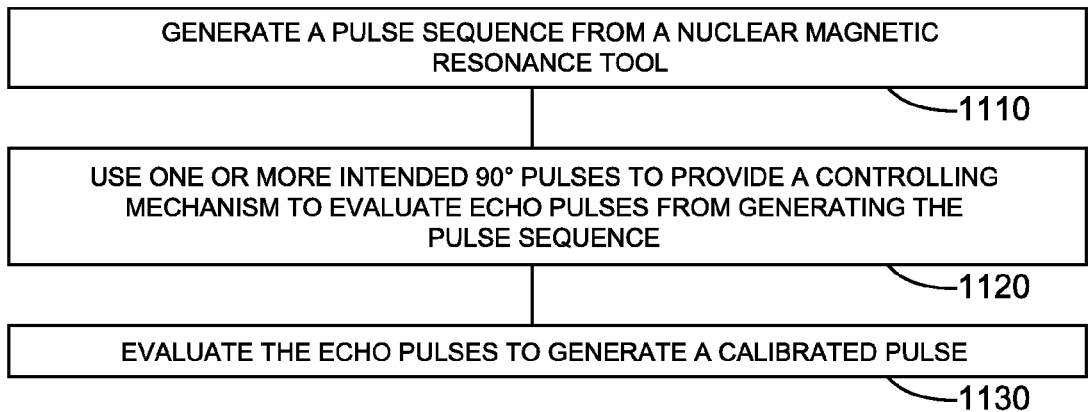
FIG. 11 shows features of an example method to calibrate a nuclear magnetic resonance tool, in accordance with various embodiments.

FIG. 11 shows features of an example method to calibrate a NMR tool. At 1110, a pulse sequence is generated from a NMR tool. The pulse sequence can have an initiating intended 90° pulse, one or more additional intended 90° pulses, and a plurality of intended 180° pulses. At 1120, the one or more additional intended 90° pulses are used to provide a controlling mechanism to evaluate echo pulses from generating the pulse sequence. At 1130, the echo pulses are evaluated to generate a calibrated pulse. Evaluating the echo pulses can include generating a calibrated 90° pulse, a calibrated 180° pulse, or both a calibrated 90° pulse and a calibrated 180° pulse. Correction factors to an $E_1$ echo and an $E_2$ echo can be generated based on evaluating the echo.

Figure 12:
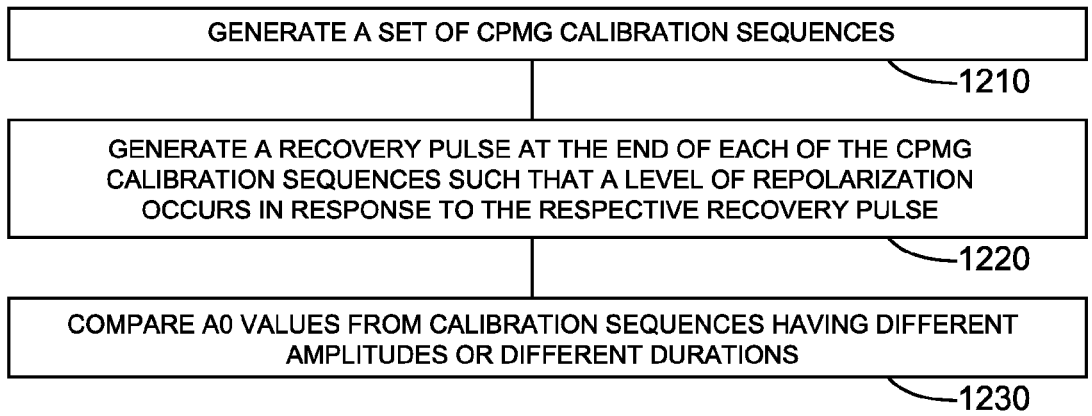
FIG. 12 shows features of an example method to calibrate a nuclear magnetic resonance tool, in accordance with various embodiments.

FIG. 12 shows features of an example method to calibrate a NMR tool. At 1210, a set of CPMG calibration sequences is generated. Each CPMG calibration sequence has a different amplitude or a different duration from other CPMG calibration sequences in the set. In an embodiment, each CPMG calibration sequence has a different amplitude from the other CPMG calibration sequences in the set. At 1220, a recovery pulse is generated at an end of each of the CPMG calibration sequences such that a level of repolarization occurs in response to the respective recovery pulse. The level of repolarization can be assigned as a percentage of full repolarization. The percentage can be ninety-seven percent. Generating the recovery pulse can include generating the recovery pulse at a time corresponding to a center of an echo following an end refocusing pulse of the respective CPMG calibration sequence. At 1230, $A_0$ values from calibration sequences having different amplitudes or different durations are compared. Each $A_0$ value can be taken to be the amplitude of an echo train at time zero corresponding to its respective CPMG calibration sequence. The method can include selecting a pulse corresponding to a largest of the $A_0$ values, the selected pulse taken as a resultant calibrated pulse.

Figure 13:
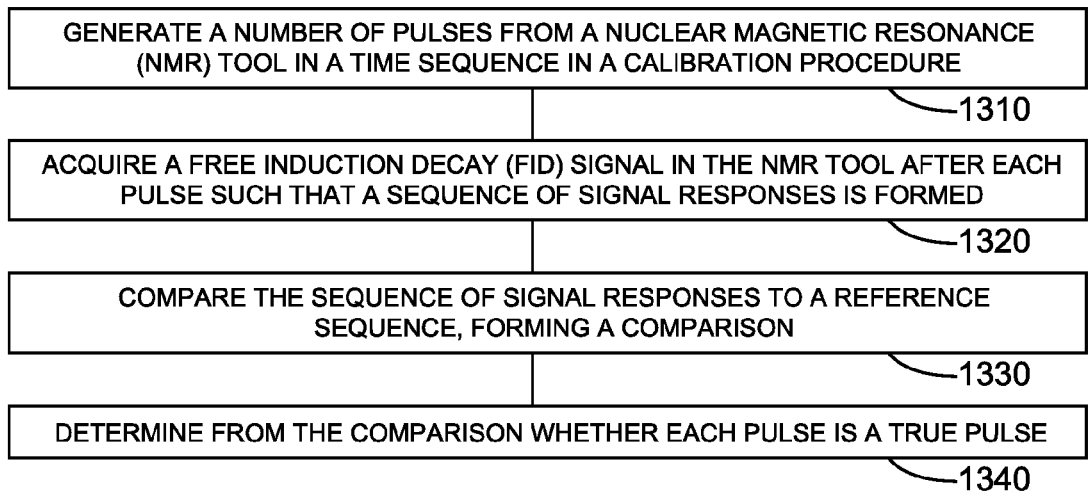
FIG. 13 shows features of an example method to calibrate a nuclear magnetic resonance tool, in accordance with various embodiments.

FIG. 13 shows features of an example method to calibrate a NMR tool. At 1310, a number of pulses is generated from a NMR tool in a time sequence in a calibration procedure. The pulses have equal transmitter amplitude. At 1320, a FID signal is acquired in the NMR tool after each pulse and before a next pulse in the time sequence such that a sequence of signal responses is formed. At 1330, the sequence of signal responses is compared to a reference sequence, forming a comparison. At 1340, a determination is made from the comparison as to whether each pulse is a true pulse. An error in the pulses can be determined based on the comparison.

The pulses can be intended 90° pulses, where the reference sequence can be an expected response pattern including maximum signal-0-negative maximum signal-0. The number of values in the pattern can equal to the number of pulses. The number of pulses can be greater than or equal to four. In an embodiment, the number of pulses is four in number.

The pulses can be intended 180° pulses, where the reference sequence can be an expected response pattern of a number of values, each value equals 0. The number of values in the pattern can be equal to the number of pulses. The number of pulses can be greater than or equal to four. In an embodiment, the number of pulses is four in number.

In an embodiment, the method can include generating a set of pulses different from another set of pulses, in response to a comparison; generating the set of pulses from the NMR tool in a time sequence for the set, the pulses of the set having equal transmitter amplitude; acquiring a FID signal in the NMR tool after each pulse of the set and before a next pulse of the set in the time sequence such that a set of signal responses is formed; comparing the set of signal responses to the reference sequence, forming a comparison of the set; and determining from the comparison of the set whether each pulse of the set is a true pulse. Each of the pulses can be assigned as calibrated pulses if the comparison results in a value less than an error threshold.

In an embodiment, the method can include performing an optimization scheme by: generating a number of sets of pulses, the pulses of each set varying in current or duration from the pulses of the other sets; generating the pulses of each set from the NMR tool, each set operated on independent of the other sets; acquiring a FID signal in the NMR tool after each pulse of each respective set and before a next pulse of the respective set in the time sequence such that a sequence of signal responses for each set is formed; and operating on the sequence of signal responses to determine an optimal calibration pulse. Operating on the sequence of signal responses can include using a search technique on the sequence of signal responses for each set to determine the optimal calibration pulse.

Figure 14:
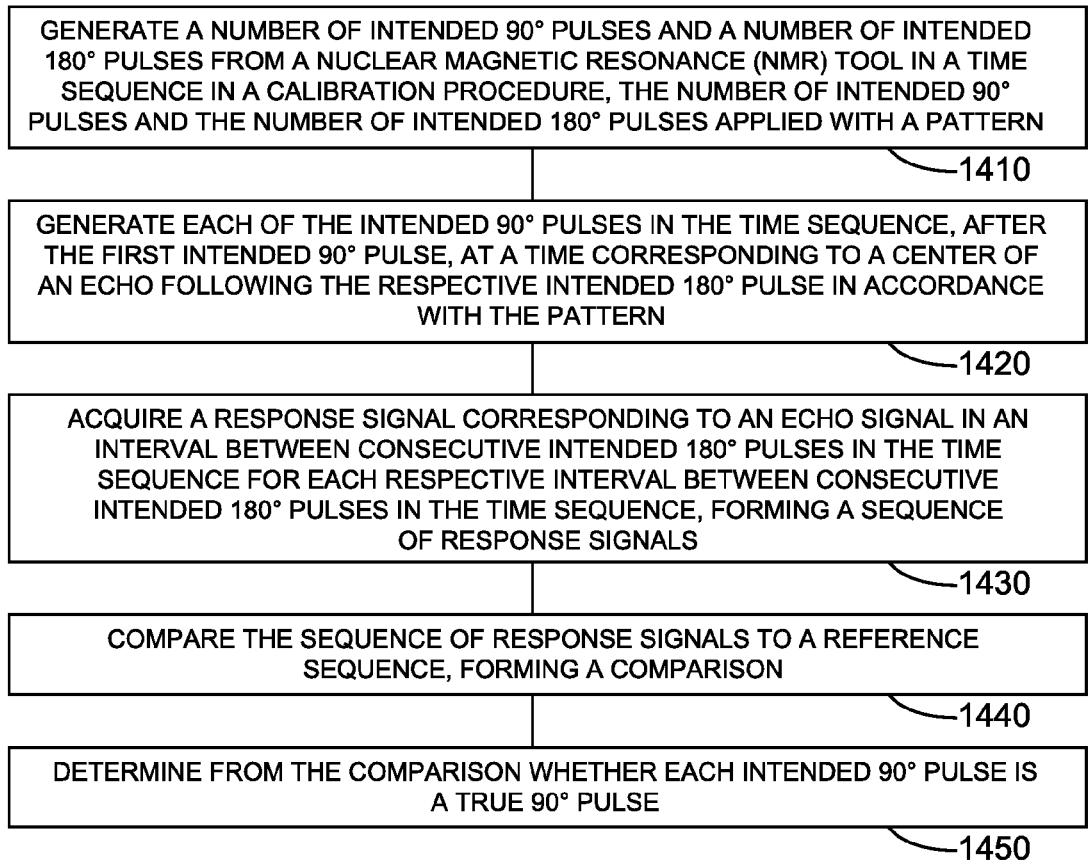
FIG. 14 shows features of an example method to calibrate a nuclear magnetic resonance tool, in accordance with various embodiments.

FIG. 14 shows features of an example method to calibrate a NMR tool. At 1410, a number of intended 90° pulses and a number of intended 180° pulses are generated from the NMR tool in a time sequence in the calibration procedure. The number of intended 90° pulses and the number of intended 180° pulses can be applied with a pattern including a first intended 90° pulse followed by a first intended 180° pulse followed by a second intended 180° pulse followed by a second intended 90° pulse with the second intended 90° pulse operable to be a beginning of the pattern repeated. At 1420, each of the intended 90° pulses in the time sequence, after the first intended 90° pulse, is generated at a time corresponding to a center of an echo following the respective intended 180° pulse in accordance with the pattern. At 1430, a response signal corresponding to an echo signal in an interval between consecutive intended 180° pulses in the time sequence is acquired for each respective interval between consecutive intended 180° pulses in the time sequence, forming a sequence of response signals. At 1440, the sequence of response signals is compared to a reference sequence, forming a comparison. The reference sequence can be an expected response pattern including maximum signal-0-negative maximum signal-0, the number of intended 90° pulses being greater than or equal to three. At 1450, a determination from the comparison can be made as to whether each intended 90° pulse is a true 90° pulse.

In an embodiment, the method can include generating a number of sets of pulses, the pulses of each set varying in current or duration from the pulses of the other sets, each set including a number of intended 90° pulses and a number of intended 180° pulses; generating, for each set, the number of intended 90° pulses and the number of intended 180° pulses from the NMR tool in a time sequence according to the pattern; forming, for each set, a sequence of response signals corresponding to an echo signal in an interval between consecutive intended 180° pulses in the time sequence for each respective interval between consecutive intended 180° pulses in the time sequence; and using an optimization technique to the sequences of response signals to determine substantially the true 90° pulse. For each respective interval, forming the sequence of response signals can include forming a sequence of values of peaks of the echo signals or a sequence of values of integrations of the echo signals.

FIG. 15 shows features of an example method to calibrate a NMR tool. At 1510, a number of pulse sequences is generated from a NMR tool in a calibration procedure such that a pulse amplitude of each pulse sequence of the number of pulse sequences varies from a pulse amplitude of other pulse sequences of the number of pulse sequences. The pulse amplitudes of each pulse sequence are intended 180° pulses selected to determine a calibrated 180° pulse. At 1520, echoes, for each pulse sequence, of an echo train generated by the respective pulse sequence are summed such that a summed echo is formed for each pulse sequence. At 1530, the summed echoes from generating the number of pulse sequences are compared such that comparison of the summed echoes determines an identified pulse sequence, along with its pulse amplitude, having its respective summed echo closest to zero. At 1540, the amplitude of the identified pulse sequence is selected to be the calibrated 180° pulse. At 1550, the calibrated 180° pulse is used to determine a calibrated 90° pulse.

Using the calibrated 180° pulse to determine the calibrated 90° pulse can include generating a pulse sequence that provides a pattern that includes intended 90° pulse-(calibrated 180° pulse-echo)$_n$-intended 90° pulse-(calibrated 180° pulse-echo)$_n$-intended 90° pulse-(calibrated 180° pulse-echo)$_n$-intended 90° pulse-(calibrated 180° pulse-echo)$_n$, in which n is a number of times a subsequence (calibrated 180° pulse-echo) is repeated at its location in the pulse sequence. Each intended 90° pulse has the same amplitude. A determination can be performed as to whether the intended 90° pulse satisfies one or more constraints to be selected as the calibrated 90° pulse. The amplitude of the intended 90° pulse can be varied and another pulse sequence with the varied amplitude can be generated to provide the same pattern. A determination as to whether the varied intended 90° pulse satisfies constraints to be selected as the calibrated 90° pulse, can be performed for a number of iterations until an identified amplitude is selected, from the varied amplitudes, that satisfies the one or more constraints to be selected as the calibrated 90° pulse. The one or more constraints can include, for each pulse sequence generated, in which each intended 90° pulse after a first intended 90° pulse of the pulse sequence is generated at a location corresponding to a center of an echo, an echo response sequence including a substantially zero response at each sequence location corresponding to a respective intended 90° pulse in the pulse sequence, and maximal response magnitudes at sequence locations corresponding to echo locations in the pattern without an intended 90° pulse.

FIG. 16 shows features of an example method to calibrate a NMR tool. The example method can include performing an iterative procedure to calibrate the NMR tool. At 1610 in an iteration, an intended 90° pulse and an intended 180° pulse are selected, the selection having an amplitude constraint defined by an amplitude of the intended 180° pulse being twice an amplitude of the intended 90° pulse, wherein in each iteration an overall amplitude is modified changing amplitudes of the intended 90° pulse and the intended 180° pulse while maintaining the amplitude constraint. At 1620 in the iteration, a pulse sequence including the intended 90° pulse and the intended 180° pulse is generated from the NMR tool such that a pattern is provided. The pattern corresponds to the intended 90° pulse, the intended 180° pulse, and echo pulses of an echo train from generating the pulse sequence. At 1630 in the iteration, a response sequence from the echo pulses is generated. At 1640 in the iteration, the response sequence is compared to a reference response pattern. The reference response pattern can correspond to a calibrated 90° pulse and 180° pulse. At 1650 in the iteration, the process can be conducted by proceeding to a next iteration until a correct pattern of the response sequence is determined from the comparison.

The pattern from generating the pulse sequence can include intended 90° pulse-(intended 180° pulse-echo)$_n$-intended 90° pulse-(intended 180° pulse -echo)$_n$-intended 90° pulse-(intended 180° pulse-echo)$_n$-intended 90° pulse-(intended 180° pulse-echo)$_n$, in which n is a number of times a subsequence (intended 180° pulse-echo) is repeated at its location in the pulse sequence. The correct pattern can include, for each pulse sequence generated in which each intended 90° pulse after a first intended 90° pulse of the pulse sequence is generated at a location corresponding to a center of an echo, a substantially zero response at each sequence location corresponding to a respective intended 90° pulse in the pulse sequence after the first intended 90° pulse and maximal response magnitudes at sequence locations corresponding to echo locations in the pattern without an intended 90° pulse.

Figure 17:
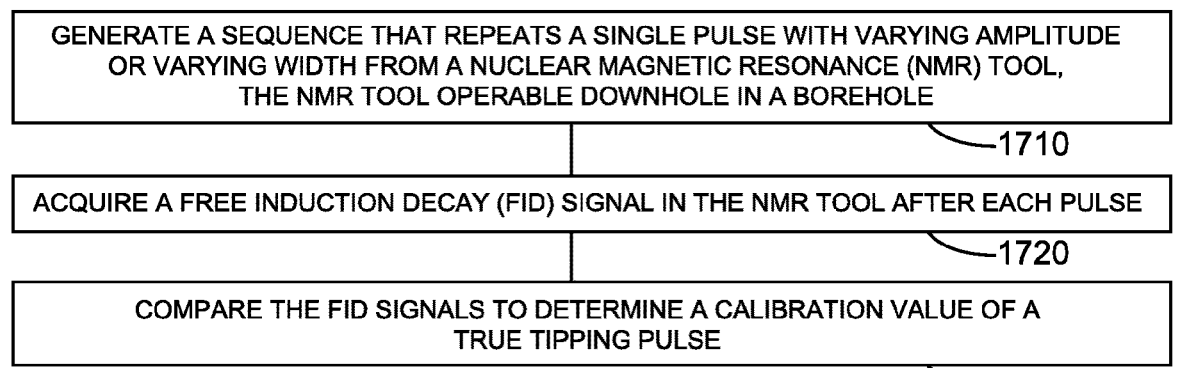
FIG. 17 shows features of an example method to calibrate a nuclear magnetic resonance tool, in accordance with various embodiments.

FIG. 17 shows features of an example method to calibrate a NMR tool. At 1710, a sequence that repeats a single pulse with varying amplitude or varying width is generated from the NMR tool, the NMR tool operable downhole in a borehole. At 1720, a FID signal is acquired in the NMR tool after each pulse. At 1720, the FID signals are compared to determine a calibration value of a true tipping pulse. Comparing the FID signals can include determining a FID signal that is a maximum of the FID signals prior to a first nullity of the acquired FID signals in a time sequence.

The method can further include generating additional sequences from the NMR tool, each sequence of the additional sequences being a sequence that repeats a single pulse with varying amplitude or varying width; acquiring a FID signal in the NMR tool after each pulse for each sequence of the additional sequences; identifying, for the sequence and for each sequence of the additional sequences, a FID signal that is a maximum of the FID signals prior to a first nullity of the acquired FID signals in a time sequence, providing a set of the identified FID signal; and determining, from the set, an optimal identified FID signal to provide a calibrated 90° tipping pulse. Comparing the FID signals can include Fourier transforming each of the FID signals and comparing the Fourier transformed signals.

In various embodiments, components of a system operable to conduct calibration of nuclear magnetic resonance tools, as described herein or in a similar manner, can be realized in instruction-based implementations, hardware, or combinations of hardware and instruction-based implementations. These implementations can include a machine-readable storage device having machine-executable instructions stored thereon, such as a computer-readable storage device having computer-executable instructions, which, when performed by a machine, cause the machine to perform operations, the operations comprising operations identical to or similar to any of the processes discussed herein, combinations of these processes, or all of the processes discussed herein. Executed instructions can also include instructions to operate a tool having one or more transmitters and one or more receivers of a nuclear magnetic resonance tool to generate tipping pulses, refocusing pulses, and recovery pulses in accordance with the teachings herein. The instructions can include instructions to provide data to a processing unit such that the processing unit conducts one or more processes to evaluate signals, data, or signals and data to conduct calibration procedures. Further, a machine-readable storage device, herein, is a physical device that stores data represented by physical structure within the device. Examples of machine-readable storage devices include, but are not limited to, read only memory (ROM), random access memory (RAM), a magnetic disk storage device, an optical storage device, a flash memory, and other electronic, magnetic, and/or optical memory devices.

In various embodiments, a system can comprise a nuclear magnetic resonance tool and a control unit coupled to the nuclear magnetic resonance tool to control the nuclear magnetic resonance tool to perform operations to perform calibration of the nuclear magnetic resonance tool.

Figure 18:
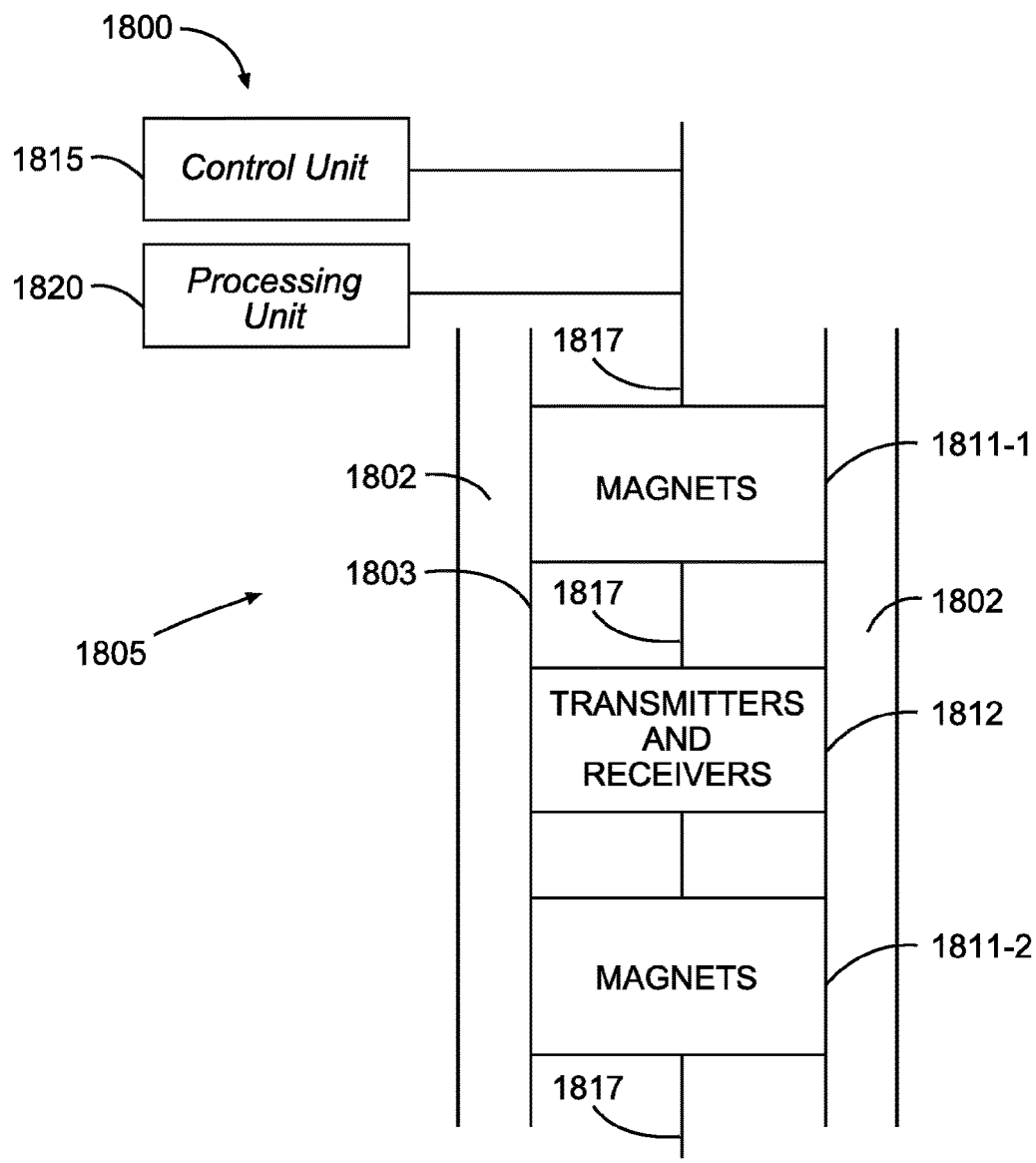
FIG. 18 depicts a block diagram of features of an example nuclear magnetic resonance tool operable in a borehole, in accordance with various embodiments.

FIG. 18 shows a block diagram of an example embodiment of a system 1800 structured to determine properties of a region of a borehole 1802 subject to nuclear magnetic resonance measurements. The system 1800 includes a nuclear magnetic resonance tool 1805 having a tool structure 1803, a control unit 1815, and a processing unit 1820. The NMR tool 1805 can be calibrated in accordance with techniques identical to or similar to procedures discussed herein. The tool structure 1803 has an arrangement of magnets 1811-1 and 1811-2 and transmitters and receivers 1812 under the control of control unit 1815. The transmitters and receivers 1812 can be realized as transceivers. These transmitters and receivers 1812 may be arranged with respect to a longitudinal axis 1817 of the tool structure 1803, though they need not be arranged relative to the longitudinal axis 1817. The control unit 1815 can be operable to manage generation and collection of signals from the one or more transmitters and receivers 1812. The generation of signals can include generating a number of echo train sequences. Each echo train sequence can include a tipping pulse, a sequence of n refocusing pulses, an end refocusing pulse, and a recovery pulse added following the end refocusing pulse. These pulses can include a 90 degree tipping pulse, 180 degree refocusing pulses, and a 90 degree recovery pulse. The control unit 1814 can selectively generate tipping, refocusing, and recovery pulses at other orientations. The processing unit 1820 of the system 1800 can be structured to process the received signals to determine properties of the region of the borehole 1802 investigated by the nuclear magnetic resonance tool 1805. The nuclear magnetic resonance tool 1805 can be structured with the processing unit 1820 and the control unit 1815 integrated with the tool structure 1803 or structured as distributed components. Distributed components can include components housed on the surface at a drilling location or downhole. In addition, the processing unit 1820 and the control unit 1815 can be realized as an integrated unit housed on the surface at a drilling location or downhole.

Figure 19:
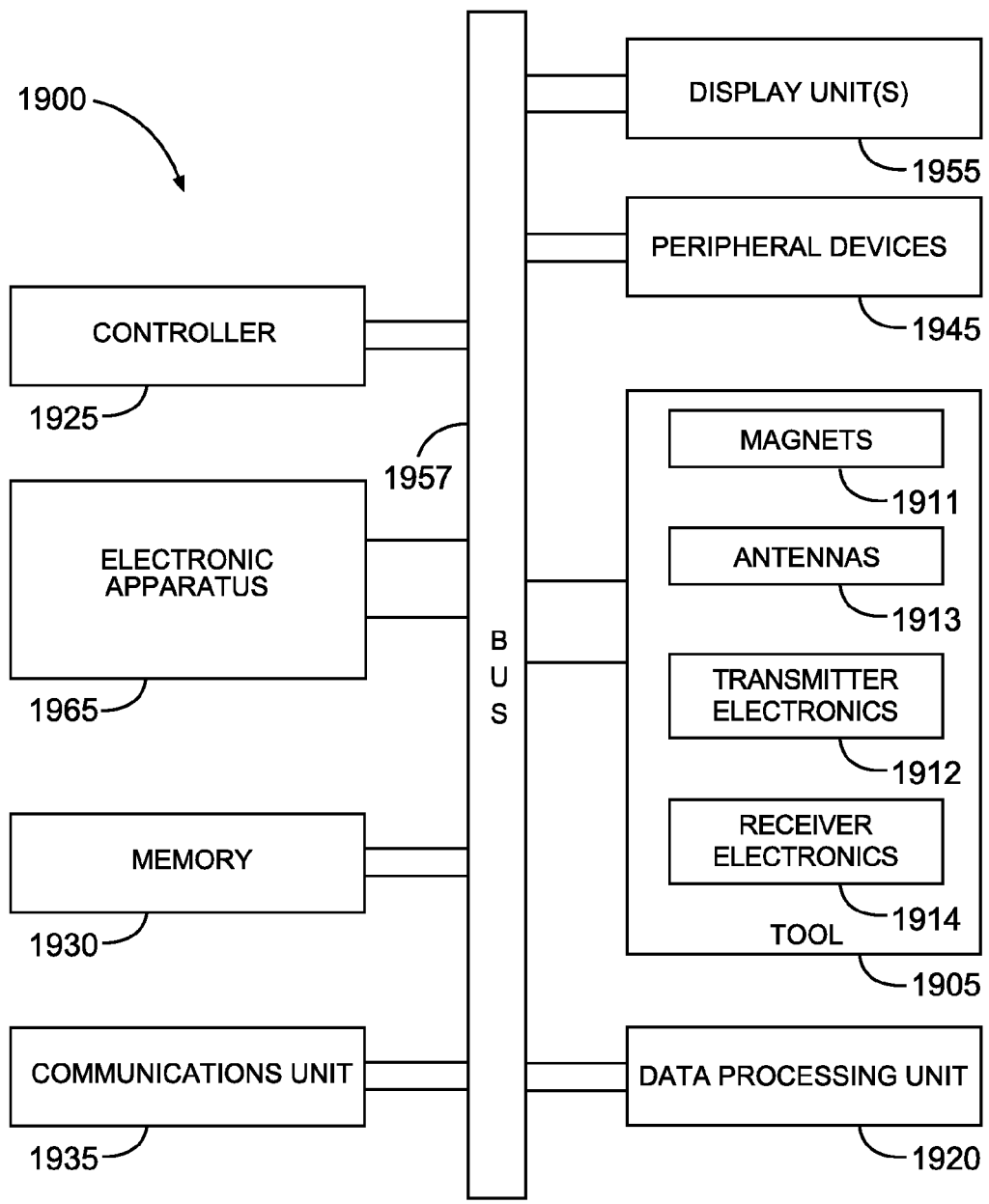
FIG. 19 depicts a block diagram of features of an example system operable in calibration of a nuclear magnetic resonance tool, in accordance with various embodiments.

FIG. 19 depicts a block diagram of features of an example embodiment of a system 1900 operable to perform calibration techniques on a NMR tool 1905, as described herein or in a similar manner. The system 1900 can include a NMR tool 1905 having an arrangement of magnets 1911, antenna(s) 1913, transmitter electronics 1912, and receiver electronics 1914. The system 1900 can be configured to operate in accordance with the teachings herein.

The system 1900 can include a controller 1925, a memory 1930, an electronic apparatus 1965, and a communications unit 1935. The memory 1930 can be structured to include a database. The controller 1925, the memory 1930, and the communications unit 1935 can be arranged to operate as a processing unit to control operation of the transmitter electronics 1912 and the receiver electronics 1914 and to perform operations on the signals collected by the receiver electronics 1914 to conduct calibration processes of the NMR tool 1905. A processing unit 1920, structured to conduct calibration processes, can be implemented as a single unit or distributed among the components of the system 1900 including electronic apparatus 1965. The controller 1925 and the memory 1930 can operate to control activation of the transmitter electronics 1912 to generate echo train sequences and recovery pulses. The controller 1925 and the memory 1930 can operate to control selection of the receiver electronics 1914 in the tool 1905 and to manage processing schemes. The controller 1925, the memory 1930, and other components of the system 1900 can be configured, for example, to operate similar to or identical to the components discussed herein or similar to or identical to any of methods discussed herein.

The system 1900 can also include a bus 1927, where the bus 1927 provides electrical conductivity among the components of the system 1900. The bus 1927 can include an address bus, a data bus, and a control bus, each independently configured or in an integrated format. The bus 1927 can be realized using a number of different communication mediums that allows for the distribution of components of the system 1900. Use of the bus 1927 can be regulated by the controller 1925. Bus 1927 can include a communications network.

In various embodiments, the peripheral devices 1945 can include additional storage memory and other control devices that may operate in conjunction with the controller 1925 and the memory 1930. In an embodiment, the controller 1925 can be realized as a processor or a group of processors that may operate independently depending on an assigned function. The system 1900 can include display unit(s) 1955, which can be used with instructions stored in the memory 1930 to implement a user interface to monitor the operation of the tool 1905 or components distributed within the system 1900.

Figure 20:
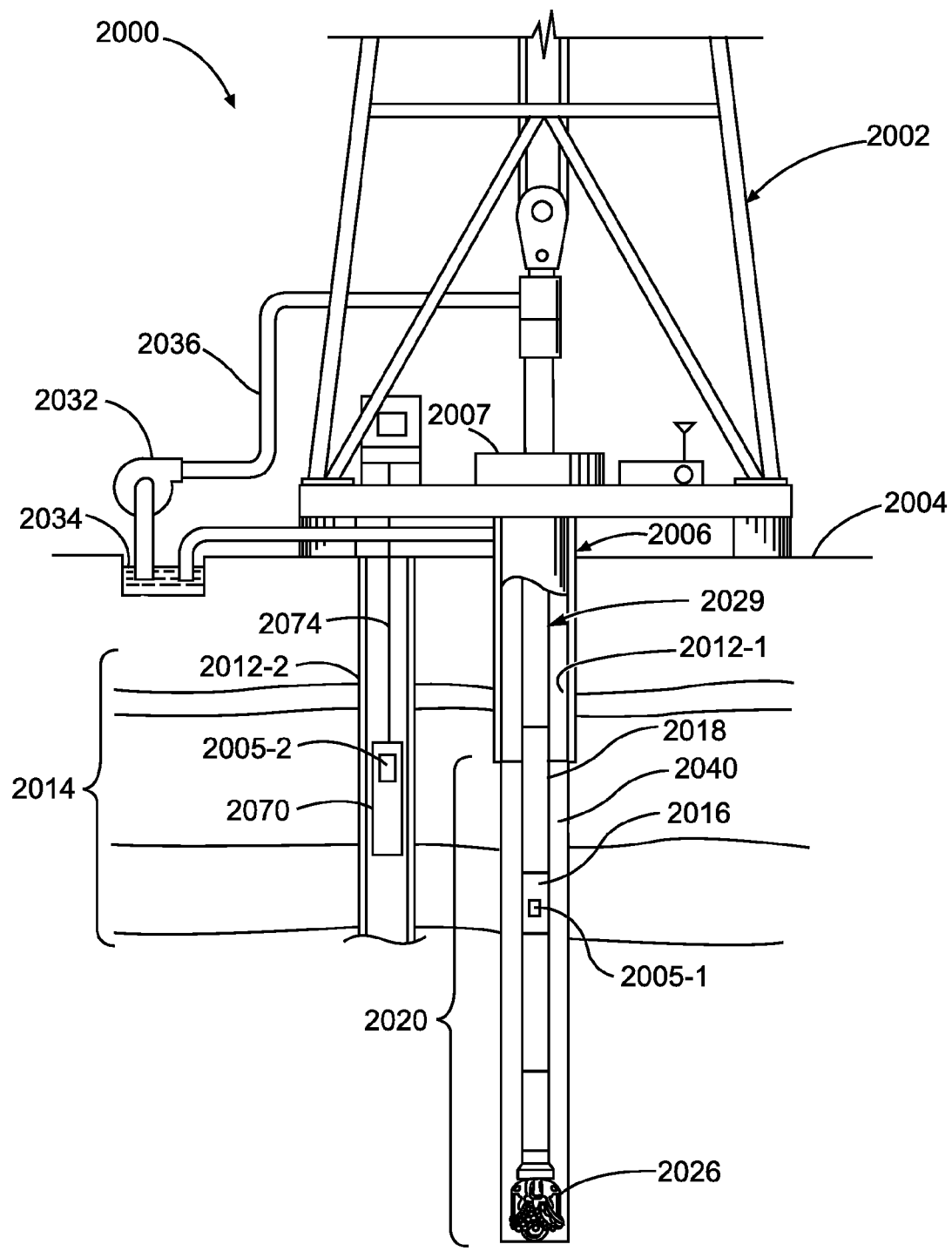
FIG. 20 depicts an example system at a drilling site, where the system includes a tool configured with a nuclear magnetic resonance tool, in accordance with various embodiments.

FIG. 20 depicts an embodiment of a system 2000 at a drilling site, where the system 2000 includes a tool 2005-1, 2005-2, or both 2005-1 and 2005-2 having a nuclear magnetic resonance tool calibrated in a technique identical to or similar to one or more techniques discussed above. The tools 2005-1, 2005-2, or both 2005-1 and 2005-2 can be distributed among the components of system 2000. The tools 2005-1 and 2005-2 can be realized in a similar or identical manner to arrangements of control units, magnets, transmitters, receivers, and processing units discussed herein. The tool 2005-1 and 2005-2 can be structured, fabricated, and calibrated in accordance with various embodiments as taught herein.

System 2000 can include a drilling rig 2002 located at a surface 2004 of a well 2006 and a string of drill pipes, that is, drill string 2029, connected together so as to form a drilling string that is lowered through a rotary table 2007 into a wellbore or borehole 2012-1. Drilling rig 2002 can provide support for drill string 2029. Drill string 2029 can operate to penetrate rotary table 2007 for drilling the borehole 2012-1 through subsurface formations 2014. Drill string 2029 can include drill pipe 2018 and a bottom hole assembly 2020 located at the lower portion of drill pipe 2018.

The bottom hole assembly 2020 can include a drill collar 2016 and a drill bit 2026. Drill bit 2026 can operate to create borehole 2012-1 by penetrating the surface 2004 and the subsurface formations 2014. Bottom hole assembly 2020 can include tool 2005-1 attached to drill collar 2016 to conduct NMR measurements to determine formation parameters. Tool 2005-1 can be structured for an implementation as a measurement while drilling (MWD) system such as a logging while drilling (LWD) system. The housing containing tool 2005-1 can include electronics to initiate NMR measurements and to collect measurement signals. Such electronics can include a data processing unit to provide analysis of formation parameters over a standard communication mechanism for operating in a well. Alternatively, electronics can include a communications interface to provide measurement signals collected by tool 2005-1 to the surface over a standard communication mechanism for operating in a well, where these measurements signals can be analyzed at a data processing unit at the surface to provide analysis of formation parameters.

During drilling operations, drill string 2029 can be rotated by rotary table 2007. In addition to, or alternatively, the bottom hole assembly 2020 can also be rotated by a motor (e.g., a mud motor) that is located downhole. Drill collars 2016 can be used to add weight to drill bit 2026. Drill collars 2016 also can stiffen the bottom hole assembly 2020 to allow the bottom hole assembly 2020 to transfer the added weight to drill bit 2026, and in turn, assist drill bit 2026 in penetrating surface 2004 and subsurface formations 2014.

During drilling operations, a mud pump 2032 can pump drilling fluid (sometimes known by those of skill in the art as "drilling mud") from a mud pit 2034 through a hose 2036 into drill pipe 2018 and down to drill bit 2026. The drilling fluid can flow out from drill bit 2026 and be returned to the surface 2004 through an annular area 2040 between drill pipe 2018 and the sides of the borehole 2012-1. The drilling fluid may then be returned to mud pit 2034, where such fluid is filtered. In some embodiments, the drilling fluid can be used to cool drill bit 2026, as well as to provide lubrication for drill bit 2026 during drilling operations. Additionally, the drilling fluid may be used to remove subsurface formation 2014 cuttings created by operating drill bit 2026.

In various embodiments, tool 2005-2 may be included in a tool body 2070 coupled to a logging cable 2074 such as, for example, for wireline applications. The tool body 2070 containing the tool 2005-2 can include electronics to initiate NMR measurements and to collect measurement signals. Such electronics can include a data processing unit to provide analysis of formation parameters over a standard communication mechanism for operating in a well. Alternatively, electronics can include a communications interface to provide measurement signals collected by tool 2005-2 to the surface over a standard communication mechanism for operating in a well, where these measurements signals can be analyzed at a data processing unit at the surface to provide analysis of formation parameters. The logging cable 2074 may be realized as a wireline (multiple power and communication lines), a mono-cable (a single conductor), and/or a slick-line (no conductors for power or communications), or other appropriate structure for use in the borehole 2012.

Although specific embodiments have been illustrated and described herein, it will be appreciated by those of ordinary skill in the art that any arrangement that is calculated to achieve the same purpose may be substituted for the specific embodiments shown. Various embodiments use permutations and/or combinations of embodiments described herein. It is to be understood that the above description is intended to be illustrative, and not restrictive, and that the phraseology or terminology employed herein is for the purpose of description. Combinations of the above embodiments and other embodiments will be apparent to those of skill in the art upon studying the above description.

What is claimed is:

1. A method for calibrating nuclear magnetic resonance (NMR) tool pulses comprising:
generating pulse sequences from a transmitter on a NMR tool, wherein each pulse sequence comprises an initiating intended 90 degree pulse, one or more additional intended 90 degree pulses, and a plurality of intended 180 degree pulses, wherein one or more amplitudes of the intended 90 degree pulses and the intended 180 degree pulses of each pulse sequence varies among the pulses sequences;
acquiring a respective sequence of response signals from a receiver attached to the NMR tool for each pulse sequence, wherein the respective sequence of response signals is acquired after each generation of the one or more additional intended 90 degree pulses of the pulse sequence associated with the respective sequence of response signals; and
generating a calibrated pulse based on the sequences of response signals from the pulse sequences, wherein the calibrated pulse is at least one of a calibrated 90 degree pulse and a calibrated 180 degree pulse.

2. The method of claim 1, wherein generating the calibrated pulse comprises generating correction factors to an $E_1$ echo and an $E_2$ echo.

3. The method of claim 1, wherein generating the pulse sequences comprises:
generating a set of CPMG calibration sequences, wherein each of the set of CPMG calibration sequences have a different amplitude or a different pulse duration from other sequences in the set of CPMG calibration sequences; and
generating recovery pulses, wherein each respective recovery pulse of the recovery pulses is generated at an end of one of the set of CPMG calibration sequences with an opposite orientation as the initiating intended 90 degree pulse;
wherein generating the calibrated pulse comprises:
obtaining $A_0$ values from calibration sequences having different amplitudes or different durations, each $A_0$ value being an amplitude of an echo train at time zero corresponding to its respective CPMG calibration sequence; and
comparing the $A_0$ values.

4. The method of claim 2, further comprising selecting a selected pulse corresponding to a greatest of the $A_0$ values, the selected pulse taken as a resultant calibrated pulse.

5. The method of claim 1, wherein generating the calibrated pulse comprises generating the calibrated pulse based a comparison between a reference sequence and the sequence of response signals.

6. The method of claim 1, further comprising:
determining that at least one of four intended 90 degree pulses is the calibrated pulse based on a sum of signals from four time periods following the four intended 90 degree pulse s being equal to zero.

7. A method comprising:
generating a number of intended 90 degree pulses and a number of intended 180 degree pulses from a nuclear magnetic resonance (NMR) tool in a time sequence in a calibration procedure, the number of intended 90 degree pulses and the number of intended 180 degree pulses applied with a pattern comprising a first intended 90 degree pulse followed by a first intended 180 degree pulse followed by a second intended 180 degree pulse followed by a second intended 90 degree pulse with the second intended 90 degree pulse operable to be a beginning of the pattern repeated;
generating each of the number of intended 90 degree pulses in the time sequence, after the first intended 90 degree pulse, at a time corresponding to a center of an echo following the respective intended 180 degree pulse in accordance with the pattern;
acquiring a response signal corresponding to an echo signal in an interval between consecutive intended 180 degree pulses in the time sequence for each respective interval between consecutive intended 180 degree pulses in the time sequence, forming a sequence of response signals;
comparing the sequence of response signals to a reference sequence, forming a comparison; and
determining from the comparison whether each intended 90 degree pulse is a true 90 degree pulse.

8. The method of claim 7, wherein the reference sequence is an expected response pattern comprising maximum signal-0-negative maximum signal-0, the number of intended 90 degree pulses being greater than or equal to three.

9. The method of claim 7, further comprising:
generating sets of pulses, wherein each set of the sets of pulses varying in pulse current or pulse duration from other sets in the sets of pulses, each set comprising a respective set of intended 90 degree pulses and a respective set of intended 180 degree pulses;
generating, for each set, a respective number of intended 90 degree pulses and a respective number of intended 180 degree pulses from the NMR tool in a respective time sequence according to the pattern;
forming, for each set, a respective sequence of response signals corresponding to a respective echo signal in the respective interval between consecutive intended 180 degree pulses in the respective time sequence for the respective interval between consecutive intended 180 degree pulses in the respective time sequence; and
using an optimization technique for a set of sequences of response signals to determine substantially the true 90 degree pulse, wherein the set of sequences of response signals comprises each respective sequence of response signals.

10. The method of claim 7, wherein, for each respective interval, forming the sequence of response signals comprises forming a sequence of values of peaks of a set of echo signals or a sequence of values of integrations of the set of echo signals, wherein the set of echo signals comprises each echo signal between consecutive intended 180 degree pulses.

11. The method of claim 7, further comprising:
generating a number of pulse sequences, wherein a pulse amplitude of each pulse sequence of the number of pulse sequences varies from other pulse amplitudes of other pulse sequences of the number of pulse sequences, and wherein the pulse amplitude of each pulse sequence being intended 180 degree pulse amplitudes selected to determine a calibrated 180 degree pulse;
summing echoes, for each respective pulse sequence, of an echo train generated by the respective pulse sequence to form a summed echo for each respective pulse sequence, wherein a set of summed echoes comprises the summed echo for each respective pulse sequence;

comparing the set of summed echoes from generating the number of pulse sequences to determine an identified pulse sequence having its respective summed echo closest to zero and determining a pulse amplitude of the identified pulse sequence;

selecting the pulse amplitude of the identified pulse sequence to be the calibrated 180 degree pulse; and using the calibrated 180 degree pulse to determine a calibrated 90 degree pulse.

12. The method of claim 11, wherein using the calibrated 180 degree pulse to determine the calibrated 90 degree pulse comprises:

generating a second pulse sequence that provides a second pattern that comprises intended 90 degree pulse-(calibrated 180 degree pulse-echo)$_n$ -intended 90 degree pulse-(calibrated 180 degree pulse-echo)$_n$-intended 90 degree pulse-(calibrated 180 degree pulse-echo)$_n$-intended 90 degree pulse-(calibrated 180 degree pulse-echo)$_n$, in which n is a number of times a subsequence (calibrated 180 degree pulse-echo) is repeated at its location in the second pulse sequence, the intended 90 degree pulse having an amplitude fixed in the second pulse sequence;

determining whether the intended 90 degree pulse satisfies one or more constraints to be selected as the calibrated 90 degree pulse;

varying the amplitude of the intended 90 degree pulse to generate a varied intended 90 degree pulse having a varied amplitude;

generating another pulse sequence with the varied intended 90 degree pulse to provide a same pattern as the second pattern; and determining whether the varied intended 90 degree pulse satisfies constraints to be selected as the calibrated 90 degree pulse, for a number of iterations until an identified amplitude is selected, from a set of varied amplitudes, that satisfies the one or more constraints to be selected as the calibrated 90 degree pulse.

13. A system for calibrating nuclear magnetic resonance (NMR) tool pulses comprising:

a NMR tool comprising at least an electromagnetic transmitter and an electromagnetic receiver; and a machine-readable storage device having machine-executable instructions which, when performed by a machine, cause the machine to perform operations to:

generate pulse sequences from the electromagnetic transmitter of the NMR tool, wherein each pulse sequence has an initiating intended 90 degree pulse, one or more additional intended 90 degree pulses, and a plurality of intended 180 degree pulses, wherein one or more amplitudes of the intended 90 degree pulses and the intended 180 degree pulses of each pulse sequence varies among the pulses sequences;

acquire a respective sequence of response signals for each pulse sequence, wherein the respective sequence of response signals is acquired after each generation of the one or more additional intended 90 degree pulses of the pulse sequence associated with the respective sequence of response signals; and generate a calibrated pulse based on the sequences of response signals from the pulse sequences, wherein the calibrated pulse is at least one of a calibrated 90 degree pulse and a calibrated 180 degree pulse.

14. The system of claim 13, wherein operations to generate the calibrated pulse comprises operations to generate correction factors to an $E_1$ echo and an $E_2$ echo.

15. The system of claim 13, wherein operations to generate the pulse sequences is part of operations to:

generate a set of CPMG calibration sequences, wherein each of the set of CPMG calibration sequences have a different amplitude or a different pulse duration from other sequences in the set of CPMG calibration sequences; and generate recovery pulses, wherein each respective recovery pulse of the recovery pulses is generated at an end of one of the set of CPMG calibration sequences with an opposite orientation as the initiating intended 90 degree pulse; and operations to generate the calibrated pulse comprises operations to:

obtain $A_0$ values from calibration sequences having different amplitudes or different durations, each $A_0$ value being an amplitude of an echo train at time zero corresponding to its respective CPMG calibration sequence; and compare the $A_0$ values.

16. The system of claim 13, wherein the operations further comprise operations to:

generate a number of intended 90 degree pulses and a number of intended 180 degree pulses applied with a pattern comprising a first intended 90 degree pulse followed by a first intended 180 degree pulse followed by a second intended 180 degree pulse followed by a second intended 90 degree pulse with the second intended 90 degree pulse operable to be a beginning of the pattern repeated;

generate each of the number of intended 90 degree pulses in a time sequence, after the first intended 90 degree pulse, at a time corresponding to a center of an echo following the respective intended 180 degree pulse in accordance with the pattern;

acquire a response signal corresponding to an echo signal in an interval between consecutive intended 180 degree pulses in the time sequence for each respective interval between consecutive intended 180 degree pulses in the time sequence, forming the sequence of response signals;

compare the sequence of response signals to a reference sequence, forming a comparison; and determine from the comparison whether each intended 90 degree pulse is a true 90 degree pulse.

17. The system of claim 16, wherein the reference sequence is an expected response pattern comprising maximum signal-0-negative maximum signal-0, the number of intended 90 degree pulses being greater than or equal to three.

18. The system of claim 16, wherein the operations further comprise operations to:

generate sets of pulses, wherein each set of the sets of pulses vary in pulse current or pulse duration from other sets in the sets of pulses, each set comprising a respective set of intended 90 degree pulses and a respective set of intended 180 degree pulses;

generate, for each set, a respective number of intended 90 degree pulses and a respective number of intended 180 degree pulses from the NMR tool in a respective time sequence according to the pattern;

form, for each set, a respective sequence of response signals corresponding to a respective echo signal in the respective interval between consecutive intended 180 degree pulses in the respective time sequence for the respective interval between consecutive intended 180 degree pulses in the respective time sequence; and use an optimization technique for a set of sequences of response signals to determine substantially the true 90 degree pulse, wherein the set of sequences of response signals comprises each respective sequence of response signals.

19. The system of claim 16, wherein, for each respective interval, the operations include operations to form the sequence of response signals comprises operations to form a sequence of values of peaks of a set of echo signals or a sequence of values of integrations of the set of echo signals, wherein the set of echo signals comprises each echo signal between consecutive intended 180 degree pulses.

20. The system of claim 16, wherein the operations further comprise operations to:
 generate a number of pulse sequences from the NMR tool in a calibration procedure, wherein a pulse amplitude of each pulse sequence of the number of pulse sequences varies from other pulse amplitudes of other pulse sequences of the number of pulse sequences, and wherein the pulse amplitude of each pulse sequence being intended 180 degree pulse amplitudes selected to determine the calibrated 180 degree pulse;
 sum echoes, for each respective pulse sequence, of an echo train generated by the respective pulse sequence to form a summed echo for each respective pulse sequence, wherein a set of summed echoes comprises the summed echo for each respective pulse sequence;
 compare the set of summed echoes from generating the number of pulse sequences to determine an identified pulse sequence having its respective summed echo closest to zero and determine a pulse amplitude of the identified pulse sequence;
 select the pulse amplitude of the identified pulse sequence to be the calibrated 180 degree pulse; and
 use the calibrated 180 degree pulse to determine the calibrated 90 degree pulse.

21. The system of claim 13, wherein the operation to generate the calibrated pulse comprises operations to generate the calibrated pulse based a comparison between a reference sequence and the sequence of response signals.

* * * * *

UNITED STATES PATENT AND TRADEMARK OFFICE
CERTIFICATE OF CORRECTION

PATENT NO. : 10,488,486 B2
APPLICATION NO. : 14/787968
DATED : November 26, 2019
INVENTOR(S) : Rebecca Corina Jachmann and Jie Yang Page 1 of 1

It is certified that error appears in the above-identified patent and that said Letters Patent is hereby corrected as shown below:

In the Specification

Column 6, Line 5, the word -Such- should read --such--.

Column 6, Line 36, the word -forth- should read --fourth--.

Column 7, Line 50, should read --summed. The current can be modified in an iterative manner--.

Signed and Sealed this
Thirty-first Day of December, 2019

Andrei Iancu
*Director of the United States Patent and Trademark Office*